(12) United States Patent
Shaul et al.

(10) Patent No.: US 6,589,534 B1
(45) Date of Patent: Jul. 8, 2003

(54) HEPATITIS B VIRUS BINDING PROTEINS AND USES THEREOF

(75) Inventors: Yosef Shaul, Sede-Gat (IL); Romi Zemel, Tel Aviv (IL)

(73) Assignee: Yeda Research and Development Co., Ltd., Rehovot (IL)

( * ) Notice: Subject to any disclaimer, the term of this patent is extended or adjusted under 35 U.S.C. 154(b) by 0 days.

(21) Appl. No.: 09/409,096

(22) Filed: Sep. 30, 1999

(51) Int. Cl.$^7$ .............................................. A61K 39/29
(52) U.S. Cl. ............................... 424/227.1; 435/189.1; 435/139.1; 435/235.1; 514/44; 530/350; 530/390.1; 536/23.6
(58) Field of Search .............................. 530/350, 390.1; 536/23.6; 435/139.1, 235.1, 189.1; 514/44; 424/227.1

(56) References Cited

U.S. PATENT DOCUMENTS 5,872,234 A    2/1999   Bandman et al.

OTHER PUBLICATIONS

Davis, CG, "The Many faces of Epidermal Growth Factor Repeats", *The New Biologist*, 2(5):410–419, 1990.

DeMeyer et al, "Organ and Species Specificity of Hepatitus B Virus (HBV) Infection: A Revue of Literature with a Special Reference to Preferentil Attachment of HBV to Human Hepatocytes" *J. Viral Hepatitus*, 4: 145–153, 1997.

Doolittle et al, Computer–Based Characterization of Epidermal Growth Factor Precursor, *Nature*, 307(9): 558–560, 1984.

Lecka–Czernik et al, "An Overexpressed Gene Transcript in Senescent and Quiescent Human Fibroblasts Encoding a Novel Protein in the Epidermal Growth Factor–Like Repeat Family Stimulates DNA Synthesis", *Molecular and Cellular Biology*, 15(1): 120–128, 1995.

Neurath et al, "Antibodies to a Synthetic Peptide from the PreS 120–145 Region of the Hepatitus B Virus Envelop are Virus–Neutraloizing", *Vaccine*, 4: 35–37, 1986.

Neurath et al "Hepatitus B Virus Contains PreS Gene–Coded Domains", *Nature*, 315: 154–156, 1985.

Petit et al, "HepG2 Cell Binding Activities of Different Hepatitus B Virus Isolates: Inhibitory Effect of Ant–HBs and AntipreS 1(21–47)", *Virology*, 180: 483–491, 1991.

Shouval et al, "Improved Immunogenicity in Mice of a Mammalian Cell–Derived Recombinant Hepatitus B Vaccine Containing Pre–$S_1$ and Pre–$S_2$ Antigens as Compared with Conventional Yeast–Derived Vaccines", *Vaccine*, 12; 1453–1459, 1994.

*Primary Examiner*—James Housel
*Assistant Examiner*—Myron G. Hill
(74) *Attorney, Agent, or Firm*—G.E. Ehrlich Ltd.

(57) ABSTRACT

An isolated nucleic acid, a recombinant protein encoded thereby and uses thereof. The isolated nucleic acid including (a) a polynucleotide at least 60% identical to SEQ ID NOs:1, 3, 5 or portions thereof as determined using the Bestfit procedure of the DNA sequence analysis software package developed by the Genetic Computer Group (GCG) at the university of Wisconsin (gap creation penalty—50, gap extension penalty—3); (b) a polynucleotide encoding a polypeptide being at least 60 homologous with SEQ ID NOs:2, 4, 6 or portions thereof as determined using the Bestfit procedure of the DNA sequence analysis software package developed by the Genetic Computer Group (GCG) at the university of Wisconsin (gap creation penalty—50, gap extension penalty—3); or (c) a polynucleotide hybridizable with SEQ ID NOs:1, 3, 5 or portions thereof at 68° C. in 6×SSC, 1% SDS, 5×Denharts, 10% dextran sulfate, 100 μg/ml salmon sperm DNA, and $^{32}$p labeled probe and wash at 68° C. with 3×SSC and 0.1% SDS.

2 Claims, 11 Drawing Sheets

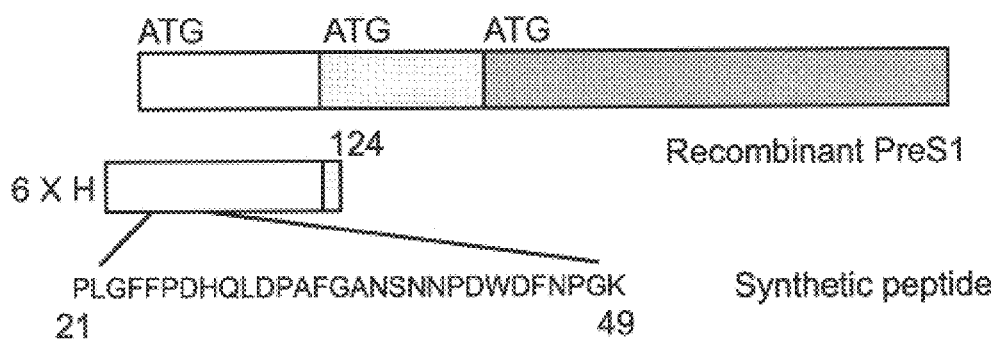
Fig. 1a
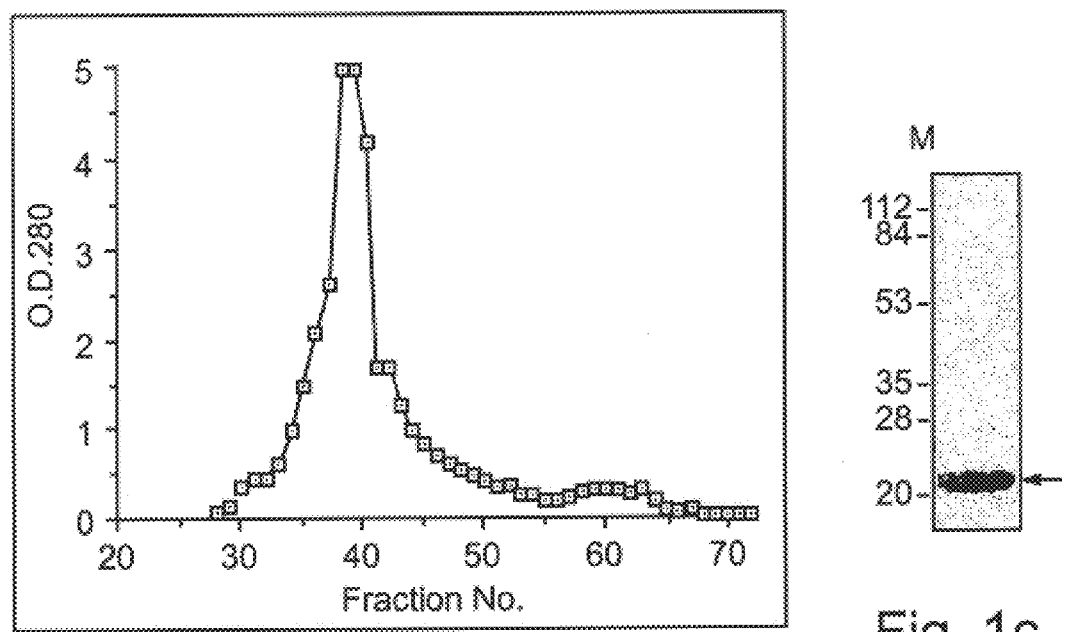
Fig. 1b
Fig. 1c

```
human  s1-5   MATSGVLPGG  GFVASAAAVA  GPEMQTGRNN  FVIRRNPADP  QRIPSNPSHR human  s1-5   IQCAAGYEQS  EHNVCQDIDE  CTAGTHNCRA  DQVCINLRGS  FACQCPPGYQ human  s1-5   KRGEQCVDID  ECTIPPYCHQ  RCVNTPGSFY  CQCSPGFQLA  ANNYTCVDIN human  s1-5   ECDASNQCAQ  QCYNILGSFI  CQCNQGYELS  SDRLNCEDID  ECRTSSYLCQ human  s1-5   YQCVNEPGKF  SCMCPQGYQV  VRSRTCQDIN  ECETTNECRE  DEMCWNYHGG human  s1-5   FRCYPRNPCQ  DPYILTPENR  CVCPVSNAMC  RELPQSIVYK  YMSIRSDRSV
up43                                                   K  YMSIRS
human  s1-5   PSDIFQIQAT  TIYANTINTF  RIKSGNENGE  FYLRQTSPVS  AMLVLVKSLS
up43                                    KSGNENGE  FYLR        AMLVLVKSL
human  s1-5   GPREHIVDLE MLTVSSIGTF RTSSVLRLTI IVGPFSF
```

UP50

MPGIKRILTV TILALCLPSP GNAQAQCTNG FDLDRQSGQC LDIDECRTIP

EACRGDMMCV NQNGGYLCHS RTNPVYRGPY SNPYSTPYSG PYPAAAPPLS

APNYPTISRP LICRFGYQMD ESNQCVDVDE CATDSHQCNP TQICINMKGG

YTCSCTDGYW LLEGQCLDID ECRYGYCQQL CANVPGSYSC TCNPGFTLNE

DGRSCQDVNE CATENPCVQT CVNTYGSFIC RCDPGYELEE DGVHCSDMDE

CSFSEFLCQH ECVNQPGTYF CSCPPGYILL DDNRSCQDIN ECEHRNHTCN

LQQTCYNLQG GFKCIDPIRC EEPYLRISDN RCMCPAENPG CRDQPFTILY

RDMDVVSGRS VPADIFQMQA TTRYPGAYYI FQIKSGNEGR EFYMRQTGPI

SATLVMTRPI KGPREIQLDL EMITVNTVIN FRGSSVIRLR IYVSQYPF

Fig. 8

|   | 1 | 2 | 3 | 4 | 5 | 6 | 7 | 8 |
|---|---|---|---|---|---|---|---|---|
| A | whole brain | amygdala | caudate nucleus | cerebellum | cerebral cortex | frontal lobe | hippocampus | medulla oblongata |
| B | occipital lobe | putamen | substantial nigra | temporal lobe | thalamus | sub-thalamic nucleus | spinal cord | |
| C | heart | aorta | skeletal muscle | colon | bladder | uterus | prostate | stomach |
| D | testis | ovary | pancreas | pituatary gland | adrenal gland | thyroid gland | salivary gland | mammary gland |
| E | kidney | liver | small-intestine | spleen | thymus | peripheral leukocyte | lymph node | bone marrow |
| F | appendix | lung | trachea | placenta | | | | |
| G | fetal brain | fetal heart | fetal kidney | fetal liver | fetal spleen | fetal thymus | fetal lung | |
| H | yeast total RNA 100 ng | yeast cRNA 100 ng | E. Coli rRNA 100 ng | E. Coli DNA 100 ng | Paly (HA) 100 ng | human C DNA 100 ng | human DNA 100 ng | human DNA 500 ng |

Fig. 9b

```
      1
UPH1  MLPCASCLPG  SLLIWALLLI  LLGSASPQDS  EEPDSYTE....  ...CTDGYTQTA
UP50  MPGIKRILTV  TILALCLPSP  GNAQAQCTNG  FDLDRQSG....  QCLDIDECRT
UP43  MLKALFLTML  TLALVKSQDT  EETITYTQCT  DGYEWDPVRQ    QCKDIDECDI
                                                                 50

51
UPH1  NCRDVNECLT  IPEACKGEMK  CTNHYGGYLC  LPRSAAVI.N   DL..........
UP50  ..........  IPEACRGDMM  CVNQNGGYLC  HSRTNPVY.R   GPYSNPYSTP
UP43  ..........  VPDACKGGMK  CVNHYGGYLC  LPKTAQIIVN   NEQPQQETQP
                                                                100

101
UPH1  ..........  ..........  ..........  ...YSGPY     PAAAPPLSAP
UP50  ..........  ..........  ..........  ..........   NY..........
UP43  AEGTSGATTG  VVAASSMATS  GVLPGGGFVA  SAAAVAGPEM   QTGRNNFVIR
                                                                150

151
UPH1  HGEGPPPPVP  PVNTQPLP--  TGYEPDDQDS  CVDVDECAQA   LHDCRPSQDC
UP50  ..........  PTISRPLICR  FGYQMDESNQ  CVDVDECATD   SHQCNPTQIC
UP43  RNPADPQRIP  SNPSHRIQCA  AGYEQSEHNV  CQDIDECTAG   THNCRADQVC
                                                                200

201
UPH1  HNLPGSYQCT  CPDGYRKIGP  ECVDIDECRY  ...RYCQHRCVN  LPGSFRCQCE
UP50  INMKGGYTCS  CTDGYWLLEG  QCLDIDECRY  ...GYCQQLCAN  VPGSYSCTCN
UP43  INLRGSFACQ  CPPGYQKRGE  QCVDIDECTI  PPYCHQRCVN   TPGSFYCQCS
                                                                250
```

Fig. 10

```
      251
UPH1  PGFQLGPNNR  SCVDVNECDM  GAPCEQRCFN  SYGTFLCRCH  QGYELHRDGF  300
UP50  PGFTLNEDGR  SCQDVNECAT  ENPCVQTCVN  TYGSFICRCD  PGYELEEDGV
UP43  PGFQLAANNY  TCVDINECDA  SNQCAQQCYN  ILGSFICQCN  QGYELSSDRL

301
UPH1  SCSDIDECSY  SSYLCQYRCV  NEPGRFSCHC  PQGYQLL.AT  RLCQDIDECE  350
UP50  HCSDMDECSF  SEFLCQHECV  NQPGTYFCSC  PPGYILLDDN  RSCQDINECE
UP43  NCEDIDECRT  SSYLCQYQCV  NEPGKFSCMC  PQGYQVVR..S  RTCQDINECE

351
UPH1  SGAHQWSEAQ  TCVNFHGGYR  CVDTNRCVEP  YIQVSENRCL  CPASNPLCRE  400
UP50  HRNHTCNLQQ  TCYNLQGGFK  CIDPIRCEEP  YLRISDNRCM  CPAENPGCRD
UP43  T...TNECREDE  MCWNYHGGFR  CYPRNPCQDP  YILTPENRCV  CPVSNAMCRE

401
UPH1  QPSSIVHRYM  TITSEAERPA  DVFQIQATSV  YPGAYNAFQI  RAGNSQGDFY  450
UP50  QPFTILYRDM  DVVSGRSVPA  DIFQMQATTR  YPGAYYIFQI  KSGNEGREFY
UP43  LPQSIVYKYM  SIRSDRSVPS  DIFQIQATTI  YANTINTFRI  KSGNENGEFY

451
UPH1  IRQINNVSAM  LVLARPVTGP  REYVLDLEMV  TMNSLMSYRA  SSVLRLTVFV  500
UP50  MRQTGPISAT  LVMTRPIKGP  REIQLDLEMI  TVNTVINFRG  SSVIRLRIYV
UP43  LRQTSPVSAM  LVLVKSLSGP  REHIVDLEML  TVSSIGTFRT  SSVLRLTIIV

501
UPH1  GAYTF
UP50  SQYPF
UP43  GPFSF
```

Fig. 10 (Cont.)

HEPATITIS B VIRUS BINDING PROTEINS AND USES THEREOF

FIELD AND BACKGROUND OF THE INVENTION

The present invention relates to a group of genes, and the proteins encoded thereby, which are capable of interfering with Hepatitis B virus (HBV) infection and to methods for identifying, purifying, isolating and characterizing related genes and gene products. The present invention further relates to isolation of soluble forms of the cellular receptor (s) for HBV on hepatocytes from bodily fluids, including, but act limited to, urine, and to purification of these soluble form binding proteins by means including, but not limited to, affinity columns. The present invention further relates to the use of these genes and their translation products to establish experimental models for HBV infection, whether in cell culture or in animals. The present invention further relates to the use of these genes and their translation products for therapeutic purposes. The present invention further relates to the use of these genes and their translation products to screen for additional binding protein interactions. The present invention further relates to the use of these genes and their translation products to prepare specific detectors of these proteins, including, but not limited to, antibodies, phage-display libraries, specific PCR primers, lectin, DNA probes, RNA probes, and non-antibody proteins for diagnostic and therapeutic purposes.

Hepatitis B virus (HBV) is an enveloped RNA virus that infects human liver and replicates via reverse-transcription of the pregenomic RNA Infected patients develop acute hepatitis, which is often self-limiting, but may develop into chronic hepatitis with high risk of liver cirrhosis and primary liver carcinoma in roughly 10% of all cases. The World Health Organization estimates that there will be 400 million carriers Worldwide in year 2000. Effective vaccines exist, but anti viral drugs with good and long term efficacy are not available. Little is known about how HBV infects liver cells and the HBV cellular receptor(s) remain unknown. Many proteins have been identified which bind to the viral envelope associated proteins, HBsAg, or related proteins, but none are considered genuine HBV receptors (reviewed in De et al., 1991 and in references cited therein). Some of these binding proteins are found in serum and some in hepatocytes. None of these molecules have been convincingly tied to infectivity, disqualifying them as genuine HBV receptors. These molecules are of three types, S binding proteins, preS2 binding proteins, and preS1 binding proteins. A brief summary of the characteristics of the three groups is provided herein.

The S binding proteins: HBsAg containing only the S protein binds to a 34-kDa liver protein, which is identified as the phospholipid-binding protein endonexin II (also known as annexin V). Endonexin II has calcium channel activity and it thought to be located primarily, but not exclusively, intracellularly. The biological significance of this remains unclear, as the observed interaction may simply reflect the known ability of endonexin 11 to bind phospholipids, which are abundant in HBsAg lipoprotein. It was subsequently demonstrated that delipidated HBsAg had a drastically diminished capacity to bind endonexin II, leading to speculation that it might play a role in a post-binding membrane fusion event.

It has also been demonstrated that plasma membranes, derived from human liver, contain apolipoprotein H (Apo H), a 46-kDa protein which binds HBsAg. This protein is a glycoprotein with four N-linked carbohydrate chains, which is present in the serum and is not an integral transmembrane protein of the hepatocyte. Its role in infection is uncertain, Moreover, it has been proven that the interaction between Apo H and HBsAg involves triglycerides and not HBV proteins. However, Apo H might play a role in delivery of the virus from the periphery to the liver.

Since binding of these molecules does not involve the preS determinant, they are unlikely to be the sole component of HBV attachment.

The preS2 binding proteins: Some researchers presumed that HBV binds to liver cells via a polymerized form of human serum albumin (pHSA) because a correlation between high viremia and the presence of a so-called pHSA receptor was observed. The preS2-specific domain does possess a pHSA binding activity, however, only pHSA from human or chimpanzee serum binds to preS2. Moreover, pHSA binds to liver cells, albeit in a non-species specific fashion. Furthermore, membranes from fresh human liver are able to bind natural HBs spheres or recombinant preS2 when they art pretreated with pHSA. These observations would suggest that the preS2 domain acts via pHSA as a species- and organ-specific attachment site of HBV except that identification of the exact binding site for pHSA within the preS2 domain is controversial.

The potential importance of pHSA binding for HBV infection has reduced by the observation that native albumin in physiologic concentrations blocks the binding of pHSA to HBsAg. This finding is especially significant considering that the minute concentration of natural pHSA present is serum is negligible when compared with the serum albumin concentration.

The N-linked glycan at the amino end of the preS2 domain has also been suggested as a potential binding site for human hepatocytes on the preS2 domain. This suggestion stems from an unusual glycan structure composed of one mannose chain and two complex chains which is liver specific and able to bind directly to HepG2 cells. Selective removal of this preS2 glycan reduces the preS2 binding by 70%.

It has also been reported that anti-idiotypic antibodies, raised against an epitope localized in the N-terminal part of preS2 protein, recognized human fibronectin, a component of the extracellular matrix. This binding is thought to be species specific because no binding was found between the preS2-associated epitopes with mouse liver. It is currently hypothesized that fibronectin may contribute to the initial binding of the circulating virus.

The preS1 binding proteins: Many researchers suggest possible roles for preS1 binding molecules in viral entry, although no conclusive evidence that these proteins play a role in permissive infection is available.

A portion of preS1, identified as being involved in attachment to HepG2 cells, is highly homologous to the Fc moiety of the α-chain of immunoglobulin A (IgA). Since IgA binds to liver plasma membranes, a common receptor for the attachment of HBV and IgA to human liver cells has bean proposed. However, known receptors for IgA do not appear to be the receptors for HBV.

Anti-idiotypic antibodies have been used to paratope anti-preS(21–47) antibodies, which may represent a mirror image of the binding site on the receptor and thus be able to react with the receptor. These antibodies reacted with a 35-kDa protein and with three other related components of 40-, 43-, and 50-kDa in HepG2 membrane extracts. The 35-kDa protein, identified as the human liver glyceraldehyde-3-phosphate-dehydrogenase (GAPD) is a key enzyme for glycolysis, and the 50-kDa protein seems to contain intrachain disulfide bonds.

In addition, 31-kDa proteins that gross-linked in vitro to a synthetic preS1 peptide (amino acids 21 to 47) has also been identified Other researchers also identified a 50-kDa protein in normal human serum which interacts with the epitopes localized within the preS1 and preS2 domains. They characterized this molecule as a glycoprotein with N-linked carbohydrate chains, which requires intact disulfide bonds in order to bind preS proteins. This 50-kDa protein blocks the binding of the preS1- and preS2-specific MAbs to HBV. This protein was detected on the surface of human hepatocytes by specific monoclonal antibodies, but not on hepatocytes from other species or in HepG2 cell membranes.

It has also been argued that the asialoglycoprotein receptor on the surface of hepatocytes a responsible for the binding of HBV, mediated by an epitope located in the preS1 domain, As the expression of the asialoglycoprotein receptor is exclusive to hepatocytes, but not species specific, the presence of HBV in extrahepatic tissue has been explained by the presence of possible asialoglycoprotein-related molecules in these non-hepatic cells.

In summary, although some of the proteins described hereinabove are able is bind virus envelope proteins, they but do not contain the molecular determinants of true receptors. Others with appropriate molecular determinants, fail to bind HBV. None of these molecules have a demonstrable role in initiating HBV infection of hepatocytes.

There is thus a widely recognized need for, and it would be advantageous to identify true HBV binding proteins, which can be effectively used as, for example, therapeutic agents.

SUMMARY OF THE INVENTION

While reducing the present invention to practice proteins were purified from concentrated human urine that bind HBsAg preS1 protein and a 29 amino-acids synthetic peptide with the sequence of HBsAg suspected to be essential for HBV infection, that satisfy a possible receptor function. Partial sequence of two of the purified proteins was determined and the corresponding cDNAs were cloned. Interestingly, the two proteins are similar and belong to the same protein family (a third protein was found in an EST library). These three proteins are membrane associated glycoproteins with EGF repeats, a characteristic structure of a very large group of cellular receptor and ligands. One of the proteins (which is referred to herein as UP50) contains also RGD motif that is known to interact with fibronectin and therefore is speculated to be a component of the extracellular matrix. This protein is expressed widely is many tissues but shows highest heel in aorta. Collectively, the data presented herein suggests that these proteins are binding proteins/ligands that may play a role in normal development in general and in HBV infection as cofactors and can therefore be used to modulate virus infection, tissue organization and cell fate and behavior.

Thus, according to one aspect of the present invention there is provided an isolated nucleic acid comprising (a) a polynucleotide at lease 60% identical to SEQ ID NOs:1, 3, 5 or portions thereof as determined using the Bestfit procedure of the DNA sequence analysis software package developed by the Genetic Computer Group (GCG) at the university of Wisconsin (gap creation penalty—50, gap extension penalty—3); (b) a polynucleotide encoding a polypeptide being at least 60% homologous with SEQ ID NOs:2, 4, 6 or portions thereof as determined using the Bestfit procedure of the DNA sequence analysis software package developed by the Generic computer Group (GCG) at the university of Wisconsin (gap creation penalty—50, gap extension penalty—3); or (c) a polynucleotide hybridizable with SEQ ID NOs:1, 3, 5 or portions thereof at 68° C. in 6×SSC, 1% SDS, 5×Denharts, 10% dextran sulfate, 100 $\mu$g/ml salmon sperm DNA, and $^{32}$p labeled probe and wash at 68° C. with 3×SSC and 0.1% SDS.

According to further features in preferred embodiments of the invention described below, the polynucleotide encodes a polypeptide capable of specifically binding HBV particles.

According to still further features in the described preferred embodiments the polynucleotide encodes a polypeptide capable of specifically binding to HBsAg preS1 protein or a portion thereof.

According to still further features in the described preferred embodiments the polynucleotide encodes a polypeptide capable of specifically binding to a polypeptide as set forth in SEQ ID NOs:8 or 9.

According to still further features in the described preferred embodiments the polynucleotide is as set forth in SEQ ID NOs:1, 3, 5 or portions thereof.

According to another aspect of the present invention there is provided a nucleic acid construct comprising the isolated nucleic acid described herein.

According to yet another aspect of the present invention there is provided a host cell comprising the isolated nucleic acid described herein.

According to still another aspect of the present invention there is provided a transgenic animal comprising the isolated nucleic acid described herein.

According to an additional aspect of the present invention there is provided an antisense molecule capable of base pairing under physiological conditions with a polynucleotide (a) at least 60% identical to SEQ ID NOs:1, 3, 5 or portions thereof as determined using the Bestfit procedure of the DNA sequence analysis software package developed by the Genetic Computer Group (GCG) at the university of Wisconsin (gap creation penalty—50, gap extension penalty—3); (b) encoding a polypeptide being at least 60% homologous with SEQ ID NOs:2, 4, 5 or portions thereof as determined using the Bestfit procedure of the DNA sequence analysis software package developed by the Genetic Computer Group (GCG) at the university of Wisconsin (gap creation penalty—50, gap extension penalty—3); or (c) hybridizable with SEQ ID NOs:1, 3, 5 or potions thereof at 68° C. in 6×SSC, 1% SDS, 5×Denharts, 10% dextran sulfate, 100 $\mu$g/ml salmon sperm DNA, and $^{32}$p labeled probe and wash at 68° C. with 3×SSC and 0.1% SDS.

According to yet an additional aspect of the present invention there is provided a pharmaceutical composition comprising, as an active ingredient, the antisense molecule described herein, and a pharmaceutically acceptable carrier.

According to still an additional aspect of the present invention there is provided a nucleic acid construct transcribable to produce the antisense molecule described herein.

According to a further aspect of the present invention there is provided a host cell comprising the antisense molecule described herein.

According to yet a further aspect of the present invention there is provided a transgenic animal comprising the antisense molecule described herein.

According to still a further aspect of the present invention there is provided a recombinant protein comprising a polypeptide (a) at least 60% homologous with SEQ ID NOs:2, 4, 6 or portions thereof as determined using the Bestfit procedure of the DNA sequence analysis software package developed by the Genetic Computer Group (GCG) at the university of Wisconsin (gap creation penalty—50, gap extension penalty—3); (b) encoded by a polynucleotide at least 60% identical to SEQ ID NOs:1, 3, 5 or portions thereof as determined using the Bestfit procedure of the DNA sequence analysis software package developed by the Genetic Computer Group (GCG) at the university of Wisconsin (gap creation penalty—50, gap extension penalty—3); or (c) encoded by a polynucleotide hybridizable with SEQ ID NOs:3, 5 or portions thereof at 68° C. in 6×SSC, 1% SDS, 5×Denharts, 10%, dextran sulfate, 100 µg/ml salmon sperm DNA, and $^{32}$p labeled probe and wash at 69° C. with 3×SSC and 0.1% SDS.

According to further features in preferred embodiments of the invention described below, the polypeptide is as set fourth in SEQ ID NOs:2, 4, 6 or portions thereof.

According to still further features in the described preferred embodiments the polypeptide is capable of specifically binding HBV particles.

According to still further features in the described preferred embodiments the polypeptide is capable of specifically binding to HBsAg pros 1 protein or a portion thereof.

According to still further features in the described preferred embodiments the polypeptide is capable of specifically binding to a polypeptide as set forth is SEQ ID NOs:8 or 9.

According to still further features in the described preferred embodiments the recombinant protein is characterized by at least one of the following (a) at least one EGF like domain; (b) at least one transmembrane domain; (c) at least one site for attachment of a hydroxyl side chain; (d) a signal peptide; (e) an RGD attachment sequence; (f) at least one glycosylation site; and (g) at least one disulfide bond.

According to another aspect of the present invention there is provided a pharmaceutical composition comprising, as an active ingredient, the recombinant protein described herein, and a pharmaceutically acceptable carrier.

According to yet another aspect of the present invention there is provided as antibody capable of specific interaction with the recombinant protein described herein.

According to still another aspect of the present invention there is provided a phage display library comprising a plurality of phages each displaying a portion of the recombinant protein described herein.

According to an additional aspect of the present invention there is provided a phage displaying at least a portion of the recombinant protein described herein.

According to yet an additional aspect of the present invention there is provided a method of isolating a polypeptide with HBV binding activity from a biological fluid, the method comprising the steps of (a) producing a purified HBV derived polypeptide; (b) binding the purified HBV derived polypeptide to a solid matrix to thereby obtain an affinity solid matrix; and (c) using the affinity solid matrix for affinity purification of the polypeptide with (HBV) binding activity from the biological fluid.

According to further features in preferred embodiments of the invention described below, the method further comprising the step of concentrating the biological fluid prior to step (c).

According to still further features in the described preferred embodiments the HBV derived polypeptide is e HBV preS1 peptide or a portion thereof.

According to still further features in the described preferred embodiments the HBV derived polypeptide is as set forth in SEQ ID NOs:8 or 9.

According to still further features is the described preferred embodiments the biological fluid is urine.

According to still further features in the described preferred embodiments the biological fluid is concentrated urine.

According to still an additional aspect of the present invention there is provided a method of inhibiting HBV attachment to a hepatic cell the method comprising the step of exposing the cell to a recombinant urine derived protein, the recombinant urine derived protein being capable of binding to a purified HBV derived polypeptide.

According to a further aspect of the present invention there is provided a pharmaceutical composition for inhibiting HBV attachment to a hepatic cell the pharmaceutical composition comprising a recombinant urine derived protein, the recombinant urine derived protein being capable of binding to a purified HBV derived polypeptide, and a pharmaceutically acceptable carrier.

According to yet a further aspect of the present invention there is provided a method of inhibiting HBV attachment to a hepatic cell the method comprising the step of loading the cell with an antisense molecule being targeted against a mRNA encoding a recombinant urine derived protein, the recombinant urine derived protein being capable of binding to a purified HBV derived polypeptide.

According to still a further aspect of the present invention there is provided a pharmaceutical composition for inhibiting HBV attachment to a hepatic cell the pharmaceutical composition comprising an antisense molecule being targeted against a mRNA encoding a recombinant urine derived protein, the recombinant urine derived protein being capable of binding to a purified HBV derived polypeptide, and a pharmaceutically acceptable carrier.

According to further features in preferred embodiments of the invention described below, the purified HBV derived polypeptide is HBsAg preS1 protein or a portion thereof.

According to still further features is the described preferred embodiments the recombinant urine derived protein includes a polypeptide selected from the group consisting of (a) at least 60% homologous with SEQ ID NOs:2, 4, 6 or portions thereof as determined using the Bestfit procedure of the DNA sequence analysis software package developed by the Genetic Computer Group (GCG) at the university of Wisconsin (gap creation penalty—50, gap extension penalty—3); (b) being encoded by a polynucleotide at least 60% identical to SEQ ID NOs:1, 3, 5 or portions thereof as determined using, the Bestfit procedure of the DNA sequence analysis software package developed by the Genetic Computer Group (GCG) at the university of Wisconsin (gap creations penalty—50, gap extension penalty—3); and (c) being encoded by a polynucleotide hybridizable with SEQ ID NOs:1, 3, 5 or portions thereof at 68° C. in 6×SSC, 1% SDS, 5×Denharts, 10% dextran sulfate, 100 µg/ml salmon sperm DNA, $^{32}$p labeled probe and wash at 68° C. with 3×SSC and 0.1% SDS.

According to still further features in the described preferred embodiments the polypeptide is as set fourth in SEQ ID NOs:2, 4, 6 or portions thereof.

According to still further features in the described preferred embodiments the polypeptide is capable of specifically binding HBV particles.

According to still further features in the described preferred embodiments the polypeptide is capable of specifically binding to HBsAg preS1 protein or a portion thereof.

According to still further features in the described preferred embodiments the polypeptide is capable of specifically binding to a polypeptide as set forth in SEQ ID NOs:8 or 9.

According to still further features in the described preferred embodiment the recombinant urine derived protein is characterized by at least one of the following (a) at least one EGF like domain; (b) at least one transmembrane domain; (c) at least one site for attachment of a hydroxyl side chain; (d) a signal peptide; (e) an RGD attachment sequence; (f) at least one glycosylation site; and (g) at least one disulfide bond.

The present invention successfully addresses the shortcomings of the presently known configurations by providing new horizons for combating HBV infections and opening new horizons in HBV research.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1a is a diagrammatic representation of the structure of the HBsAg gene and the preS1 region used for the preparation of a recombinant protein. Also shown is the sequence (SEQ ID NO:9) and position of a synthetic peptide of 29 amino acids used in the examples hereinbelow.

FIG. 1b shows a His-preS1 recombinant protein expressed in *E. coli* BL21 cells, induced with IPTG (0.1 mM) soluble fraction, purified on Ninta-affinity column, nm on a reducing SDS-PAGE (15%) gel and stained with coomassie brilliant blue. M—molecular mass as determined by a low range molecular weight standard (BioRad).

FIG. 1c shows a gel filtration purification of a synthetic peptide composed of the preS1 amino acids 21–49 (SEQ ID NO:9) in which absorbance at OD280 is plotted as a function of fraction number.

FIG. 6 shows that UP43 is identical to a protein known as S1–5. Sequences of three fragments of UP43 are identical to the published S1–5 clone (Databank accession No. AAA65590).

FIG. 8 shows the UP50 amino-acid sequence. UP50 was trypsin digested and 4 fragments were microsequenced (underlined regions). These sequences were used to clone the entire up50 cDNA, as is further detailed in the Examples section below.

FIGS. 9a and 9b show the tissue distribution of up50 mRNA. A commercial "master-blot" that contains RNA from different human tissues (9b), was hybridized to a up50 cDNA probe. The size and stringency of the dots (9a) are in correlation with the level of expression in the corresponding tissues.

FIG. 10 is a comparison of the sequence of the extended UP protein family UPH1, UP50) and UP43 (SEQ ID NOs:6, 4 and 2 respectively). The sequence of UP43. UP50 and the homologous UPH1 an compared using Bestfit procedure of the DNA sequence analysis software package developed by the Genetic Computer Grove (GCG) at the university of Wisconsin (gap creation penalty—50, gap extension penalty—3).

DESCRIPTION OF THE PREFERRED EMBODIMENTS

Figure 2:
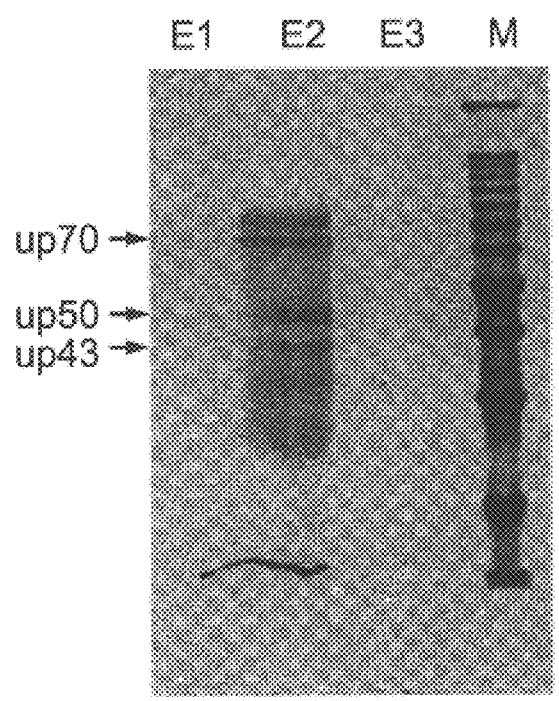
FIG. 2 demonstrates isolation of preS1 binding proteins from concentrated human urine conducted by 12% SDS-PAGE which was silver stained. Prior to loading on the gel, concentrated urine was loaded on a recombinant preS1 protein affinity column. After washing, bound proteins were eluted by low pH buffer containing: 0.2 M glycine pH 2.5, 50% PEG and 10% TWEEN20. Lanes E-1 to E-3 represent eluted fractions 1 to 3, respectively. Lane M represents a 10 kDa ladder marker. UP50 and UP43 are indicated by the left arrows.

The present invention is of a group of genes, and the proteins encoded thereby, which are capable of interfering with Hepatitis B virus (HBV) infection and of methods for identifying purifying, isolating and characterizing related genes and gene products. The present invention is further of a method for the isolation of soluble forms of the cellular receptor(s) for HBV on hepatocytes from bodily fluids, including, but not limited to, urine, and to purification of trace soluble form binding proteins by means including, but not limited to, affinity columns. The present invention is further of the use of these genes and their translation products to establish experimental models for HBV infection, whether in cell culture or in animals. The present invention is further of the use of these genes and their translation products for therapeutic purposes. The present invention is further of the use of these genes and their translation products to screen for additional ligand/receptor interactions. The present invention is further of the use of these genes and their translation products to prepare specific detectors of these proteins, including, but not limited to, antibodies, phage-display libraries, specific PCR primers, lectins, DNA probes, RNA probes, and non-antibody proteins for diagnostic and therapeutic purposes.

The principles and operation of a according to the present invention may be better understood with reference to the drawings and accompanying descriptions.

Before explaining at least one embodiment of the invention in detail, it is to be understood that the invention is not limited in its application to the details of construction and the arrangement of the components act forth in the following description or illustrated in the drawings. The invention is capable of ocher embodiments or of being practiced or carried out in various ways. Also, it is to be understood that the phraseology and terminology employed herein is for the purpose of description and should not be regarded as limiting.

While reducing the present invention to practice purified HBV derived polypeptides, representing portions of the preS1 region of HBsAg, one recombinant (SEQ ID NO:8) and one synthetic (SEQ ID NO:9), were used to create two affinity columns. These columns were used to affinity capture soluble proteins from concentrated human urine samples. Several proteins were Thus identified and some were further characterized. The proteins were trypsin digested, proteolytic portions thereof microsequenced and their corresponding cDNAs isolated and sequenced. Using ELISA approach it was found that the proteins bind HBV particles. Using GFL fusion constructs it was found that the proteins are membrane associated proteins. Using glyconase it was found that the proteins are in fact glycoproteins. Using reducing gel electrophoresis conditions it was found the proteins are characterized by disulfide bonds. Using sequence analysis programs it was found that (i) at least one of the proteins may be characterized by alternative initiation of translation; (ii) the proteins include several EGF repeats; (iii) some EGF repeats contain aspartic-acid and asparagine that undergo hydroxylation; (iv) all proteins have a transmembrane domain at the C-terminus, suggesting that they are membrane associated; (v) these also contain a signal-peptide at the N-terminus, suggesting that the N-terminus is positioned out of the cells.

Thus, according to one aspect of the present invention there is provided an isolated nucleic acid comprising (a) a polynucleotide at least 50%, at least 60%, at least 65%, at least 70%, at least 75%, at least 80%, at least 85%, at least 90%, at least 95% or preferably 95–100% identical to SEQ ID NOs:1, 3, 5 or portions thereof as determined using the Bestfit procedure of the DNA sequence analysis software package developed by the Genetic Computer Group (GCG) at the university of Wisconsin (gap creation penalty—50, gap extension penalty—3); (b) a polynucleotide encoding a polypeptide being at least 50%, at least 60%, at least 65%, at least 70%, at least 75%, at least 80%, at least 85%, at least 90%, at least 95% or preferably 95–100% homologous (identical+similar amino acids) with SEQ ID NOs:2, 4, 6 or portions thereof as determined using the Bestfit procedure of the DNA sequence analysis software package developed by the Genetic Computer Group (GCG) at the university of Wisconsin (gap creation penalty—50), gap extension penalty—3); and/or (c) a polynucleotide hybridizable with SEQ ID NOs:1, 3, 5 or portions thereof at 65, 68 or 72° C. in 6×SSC. 1% SDS, 5×Denharts, 10% dextran sulfate, 100 $\mu$g/ml salmon sperm DNA, and $^{32}$p labeled probe and wash at 65, 68 or 72° C. with 3×SSC and 0.1% SDS or in addition with 0.1×SSC and 0.1% SDS.

The above isolated nucleic acids thus include both complementary DNA (cDNA), genomic DNA and composite DNA, variants, natural mutants, induced mutants, alleles, and homologs from human and other species, including, for example, primates.

As used herein In the specification the phrase "complementary DNA" includes sequences which originally result from reverse transcription of messenger RNA using a reverse transcriptase or any other RNA dependent DNA polymerase. Such sequences can be subsequently amplified in vivo or in vitro using a DNA dependent DNA polymerase.

As used herein in the specification the phrase "genomic DNA" includes sequences which originally derive froth a chromosome and reflect a contiguous portion of a chromosome.

As used herein in the specification the phrase "composite DNA" includes sequences which are at least partially complementary and at least partially genomic. A composite sequence can include some exonal sequences required to encode the polypeptides described herein, as well as some intronic sequences interposing therebetween. The intronic sequences can be of any source, including of other genes, and typically will include conserved splicing signal sequences. Such intronic sequences may further include cis acting expression regulatory elements.

Having the isolated nucleic acids described in the Examples section that follows available, and employing conventional cloning, screening and other techniques, one can readily isolate additional cDNAs, genomic DNAs, variants, natural mutants, induced mutants, alleles, and homologs from human and other species, including, for example, primates, which relate to these nucleic acids. Such techniques are described is detail, in, for example, Molecular Cloning: A laboratory Manual" Sambrook et al., (1989); and in "Current Protocols in Molecular Biology" Volumes I–III Ausubel, R. M., ed. (1994).

Thus, this aspect of the present invention encompasses (i) polynucleotides as set forth in SEQ ID NOs:1, 3 and 5; (ii) fragments thereof; (iii) genomic sequences including same; (iv) sequences hybridizable therewith; (v) sequences homologous thereto; (vi) sequences encoding similar polypeptides with different codon usage; (vii) altered sequences characterized by mutations, such as deletion, insertion a substitution of one or more nucleotides, either naturally occurring or man induced; either randomly or in a targeted fashion.

According to a preferred embodiment of the present invention, the polynucleotide encodes a polypeptide capable of specifically binding HBV particles, to HBsAg preS1 protein or a portion thereof, e.g., SEQ ID NOs:8 or 9.

As used herein in the specification and is the claims section that follows, the term HBV particles refers to HBV assembled coat proteins, which are produced by transforming a cell with a gene or genes encoding such proteins, such that the cell produces the coat proteins and the coat proteins are integrated in the cell membrane which is thereafter used to form the HBV particles. For further details of the preparation of HBV particles the reader is referred to Shouval et al. (1994), which is incorporated herein by reference.

For many applications it is required that the isolated nucleic acid described herein will be integrated in a nucleic acid construct, such as an expression construct or an antisense construct. Such constructs are well known in the art, are commercially available and may include additional sequences, such as, for example, are or more promoter and enhancer sequences, a cloning site, one or more prokaryote or eukatyote marker genes with their associated promoters, one or more prokaryotic and/or eukaryotic origins of replication, a translation start site, a polyadenylation signal, and the like.

Thus, according to a preferred embodiment the nucleic acid construct according to this aspect of the present invention further comprising a promoter for regulating the expression of the isolated nucleic acid in a sense or antisense orientation. Such promoters are known to be cis-acting sequence elements required for transcription as they serve to bind DNA dependent RNA polymerase which transcribes sequences present downstream thereof. Such down stream sequences can be In either one of two possible orientations to result in the transcription of sense RNA which is translatable by the ribozyme machinery or antisense RNA which typically does not contain translatable sequences, yet can duplex or triplex with endogenous sequences, either mRNA or chromosomal DNA and hamper gene expression, all as further detailed hereinunder.

While the isolated nucleic acid described herein is as essential element of the invention, it is modular and can be used in different contexts. The promoter of choice that is used in conjunction with this invention a of secondary importance, and will comprise any suitable promotes. It will be appreciated by one skilled in the art, however, that it is necessary to make sure that the transcription start sites) will be located upstream of an open reading frame. In a preferred embodiment of the present invention, the promoter that is selected comprises an element that is active in the particular host calls of interest. These elements may be selected from transcriptional regulators that activate the transcription of genes essential for the survival of these cells in conditions of stress or starvation, including the heat shock proteins.

A construct according to the present invention preferably further includes an appropriate selectable marker. In a more preferred embodiment according to the present invention the construct further includes an origin of replication. In another most preferred embodiment according to the present invention the construct is a shuttle vector, which can propagate both in *E. coli* (wherein the construct comprises an appropriate selectable marker and origin of replication) and be compatible for propagation in cells, or integration in the genome, of an organism of choice. The construct according to this aspect of the present invention can be, for example, a plasmid, a bacmid, a phagemid, a cosmid, a phage, a virus or an artificial chromosome.

Alternatively, the nucleic acid construct according to this aspect of the present invention further includes a positive and a negative selection markers and may therefor be employed for selecting for homologous recombination events, including, but not limited to, homologous recombination employed in knock-in and knock-out procedures. On ordinarily skilled in the art can readily design a knock-out or knock-in constructs including both positive and negative selection genes for efficiently selecting transfected embryonic stem cells that underwent a homologous recombination event with the construct. Such cells can be introduced into developing embryos to generate chimeras, the offspring thereof can be tested for carrying the knock-out ox knock-in constructs. Knock-out and/or knock-in constructs according to the present invention can be used to further investigate the functionality of the genes/proteins described herein. Such constructs can also be used in somatic and/or germ cells gene therapy. Additional detail can be found in Fukushige, S. and Ikeda, J. E.: Trapping of mammalian promoters by Cre-lox site-specific recombination. DNA Res 3 (1996) 73–80; Bedell, M. A., Jenkins, N. A. or and Copeland, N. G.: Mouse models of human disease. Part I: Techniques or resources for genetic analysis in mice. Genes and Development 11 (1997) 1–11; Bermingham, J. J., Scherer, S. S., O'Connell, S., Arroyo, E., Kalla K. A., Powell, F. L. and Rosenfeld, M. G.: Tst-1/Oct-6/SCIP regulates a unique step in peripheral myelination and is required for normal respiration. Genes Dev 10 (1996)1751–62, which are incorporated here by reference.

According to yet another aspect of the present invention there is provided a host cell comprising the isolated nucleic acid described herein. Such a host cell can be either a prokaryote or a eukayote cell, the nucleic acid can either be integrated into the cell's genome or be extrachromosomal.

According to still another aspect of the present invention there is provided a transgenic animal comprising the isolated nucleic acid described herein. Methods of generating transgenic animals are well known in the art and are therefore not further described herein.

Such cells and animals can End utility in the propagation of HBV It will be appreciated that so for culture propagation of HBV is impractical. The cells and animals described herein can, however, be employed for propagation of the virus: as a receptor therefore is expressed by such cells or animals. In another case, where, either antisense or gene knock-out or knock-in techniques are employed, such cells and animals can be used to further study the involvement of the genes reported herein in HBV attachment.

According to an additional aspect of the present invention them is provided a pair of oligonucleotides each independently of at least 17, at least 18, at least 19, at least 20, at least 22, at least 25, at least 30 or at least 40 bases specifically hybridizable with the isolated nucleic acid described herein in an opposite orientation so as to direct exponential amplification of a portion thereof in a nucleic acid amplification reaction, such as a polymerase chain reaction. The polymerase chain reaction and other nucleic acid amplification reactions are well known in the art and require no further description herein. The pair of oligonucleotides according to this aspect of the present invention are preferably elected to have compatible melting temperatures (Tm), e.g., melting temperatures which differ by less than that 7° C., preferably less than 5° C., more preferably less than 4° C., most preferably less then 5° C., ideally between 3° C. and zero° C. Consequently, according to yet an additional aspect of the present invention there is provided a nucleic acid amplification product obtained using the pair of primers described herein. Such a nucleic acid amplification product can be isolated by gel electrophoresis of any other size based separation technique. Alternatively, such a nucleic acid amplification product can be isolated by affinity separation, either stranded affinity or sequence amity. In addition, once isolated, such a product can be further genetically manipulated by restriction, ligation and the like, to serve any one of a plurality of applications.

According to an additional aspect of the present invention there is provided an antisense molecule capably of base pairing under physiological conditions with a polynucleotide (a) at least 50%, at least 60% at least 65% at least 70%, or least 75%, at least 80%, at least 85%, at least 90%, at least 95% or preferably 95–100% identical to SEQ ID NOs:1, 3, 5 or potions thereof as determined using the Bestfit procedure of the DNA sequence analysis software package developed by the Genetic Computer Group (GCG) at the university of Wisconsin (gap creation penalty—50, gap extension penalty—3); (b) encoding a polypeptide being at least 50%, at least 60%, at least 65%, at least 70%, at least 75%, at least 80%, at least 85%, at least 90%, at least 95% or preferably 95–100% homologous with SEQ ID NOs:2, 4, 6 or portions thereof as determined using the Bestfit procedure of the DNA sequence analysis software package developed by the Genetic Computer Group (GCG) at the university of Wisconsin (gap creation penalty—50, gap extension penalty—3); or (c) hybridizable with SEQ ID NOs:1, 3, 5 or portions thereof at 65, 68 or 72° C. in 1×SSC, 1% SDS, 5×Denharts, 10% dextran sulfate, 100 µg/ml salmon sperm DNA, and $^{32}$p labeled probe and wash at 65, 68 or 72° C. with 3×SSC and 0,1% SDS or in addition with 0.1×SSC and 0.1% SDS.

Such an antisense molecule can be a single stranded DNA, RNA, or polynucleotide analog of at least 10 bases, preferably between 10 and 15, more preferably between 50 and 20 bases, most preferably, at least 17, at least 18, at least 19, at least 20, at least 22, at least 25, at least 30 or at least 40 bases.

According to still an additional aspect of the present invention there is provided a nucleic acid construct transcribable to produce the antisense molecule described herein Such a construct is further described hereinabove and can be used to generate a host cell or a transgenic animal comprising an antisense molecule as described herein.

Such an antisense oligonucleotide is readily synthesizable using solid phase oligonucleotide synthesis.

The ability of chemically synthesizing oligonucleotides and analogs thereof having a selected predetermined sequence offers means for downmodulating gent expression. Three types of gene expression modulation strategies may be considered.

At the transcription level, antisense or sense oligonucleotides or analog, that bind to the genomic DNA by strand displacement or the formation of a triple helix, may prevent transcription. At the transcript level, antisense oligonucleotides or analogs that bind target mRNA molecules lead to the enzymatic cleavage of the hybrid by intracellular RNase H. In this case, by hybridizing to the targeted mRNA, the oligonucleotides or oligonucleotide analogs provide a duplex hybrid recognized and destroyed by the RNase H enzyme. Alternatively, such hybrid formation may lead to interference with correct splicing. As a result, in both casts, the number of the target mRNA intact transcripts ready for translation is reduced or eliminated. At the translation level, antisense oligoucleotides or analogs that bind target mRNA molecules prevent, by steric hindrance, binding of essential translation factors (ribosomes), to the target mRNA, a phenomenon known in the art as hybridization arrest, disabling the translation of such mRNAs.

Thus, antisense sequences, which as described hereinabove may arrest the expression of any endogenous and/or exogenous gene depending on their specific sequence, attracted much attention by scientists and pharmacologists who were devoted at developing the antisense approach into a new pharmacological tool.

For example, several antisense oligonucleotides have been shown to arrest hematopoietic cell proliferation, growth, entry into the S phase of the cell cycle, reduced survival and prevent receptor mediated responses.

For efficient in vivo inhibition of gene expression using antisense oligonucleotides or analogs, the oligonucleotides or analogs must fulfill the following requirements (i) sufficient specificity in binding to the target sequence; (ii) solubility in water; (iii) stability against infra- and extracellular nucleases; (iv) capability of penetration through the cell membrane; and (v) when used to treat an organism, low toxicity.

Unmodified oligonucleotides are typically impractical for use as antisense sequences since they have shore in vivo half-lives, during which they are degraded rapidly by nucleases. Furthermore, they are difficult to prepare in more than milligram quantities. In addition, such oligonucleotides are poor cell membrane penetraters.

Thus it is apparent that in order to meet all the above listed requirements; oligonucleotide analogs need to be devised in a suitable manner. Therefore, an extensive search for modified oligonucleotides has been initiated.

For example, problems arising in connection with double-stranded DNA (dsDNA) recognition through triple helix formation have been diminished by a clever "switch back" chemical linking, whereby a sequence of polypurine on one strand is recognized, and by "switching back", a homopurine sequence on the other strand can be recognized. Also, good helix formation has been obtained by using artificial bases, thereby improving binding conditions with regard to ionic strength and pH.

In addition, in order to improve half-life as well as membrane penetration, a large number of variations in polynucleotide backbones have been done, nevertheless with little success.

Oligonucleotides can be modified either in the base, the sugar or the phosphate moiety. These modifications include, for example, the use of methylphosphonates, monothiophosphates, dithiophosphates, phosphoramidates, phosphate esters, bridged phosphorothioates, bridged phosphoramidates, bridged methylenephosphonates, dephospho internucleotide analogs with siloxane bridges, carbonate bridges, carboxymethyl ester badges, carbonate bridges, carboxymethyl ester bridges, acetamide bridges, carbamate bridges, thioether bridges, sulfoxy bridges, sulfono bridges, various "plastic" DNAs, α-anomeric bridges end borane derivatives.

International patent application WO 89/12060 discloses various building blocks for synthesizing oligonucleotide analogs, as well as oligonucleotide analogs formed by joining such building blocks in a defined sequence. The building blocks may be either "rigid" (i.e., containing a ring structure) or "flexible" (i.e., lacking a ring structure). In both cases, the building blocks contain a hydroxy group and a mercapto group, through which the building blocks are said to join to form oligonucleotide analogs. The linking moiety in the oligonucleotide analogs is selected from the group consisting of sulfide (—S—), sulfoxide (—SO—), and sulfone (—SO$_2$—).

International patent application WO 92/20702 describe an acyclic oligonucleotide which includes a peptide backbone on which any selected chemical nucleobases or analogs are stringed and serve as coding characters as they do in natural DNA or RNA. These new compounds, known as peptide nucleic acids (PNAs), are not only more stable in cells than their natural counterparts, but also bind natural DNA and RNA 50 to 100 times more tightly than the natural nucleic acids cling to each other. PNA oligomers can be synthesized from the four protected monomers containing thymine, cytosine, adenine and guanine by Merrifield solid-phase peptide synthesis. In order to increase solubility in water and to prevent aggregation, a lysine amide group is placed at the C-terminal region.

Thus, in one aspect antisense technology requires pairing of messenger RNA with an oligonucleotide to form a double helix that inhibits translation. The concept of antisense-mediated gene therapy was already introduced in 1978 for cancer therapy. This approach was based on certain genes that are crucial in cell division and growth of cancer cells. Synthetic fragments of genetic substance DNA can achieve this goal. Such molecules bind to the targeted gene molecules in RNA of tumor cells, thereby inhibiting the translation of the genes and resulting in dysfunctional growth of these cells. Other mechanisms has also been proposed. These strategies have been used, with same success in treatment of cancers, as well as other illnesses, including viral and other infectious diseases. Antisense oligonucleotides are typically synthesized in lengths of 13–30 nucleotides. The life span of oligonucleotide molecules is blood is rather short. Thus, they have to be chemically modified to prevent destruction by ubiquitous nucleases present a the body. Phosphorothioates are very widely used modification in antisense oligonucleotide ongoing clinical trials. A new generation of antisense molecules consist of hybrid antisense oligonucleotide with a central portion of synthetic DNA while four bases on each end have been modified with 2'O-methyl ribose to resemble RNA. In preclinical studies in laboratory animals, such compounds have demonstrated greater stability to metabolism in body tissues and as improved safely profile when compared with the first-generation unmodified phosphorothioate. Dozens of other nucleotide analogs have also been tested in antisense technology.

RNA oligonucleotides may also be used for antisense inhibition as they form a stable RNA-RNA duplex with the target, suggesting efficient inhibition However, due to their low stability RNA oligonucleotides are typically expressed inside the cells using vectors designed for this purpose. This approach is favored when attempting to target a mRNA that encodes an abundant and long-lived protein.

Recent scientific publications have validated the efficacy of antisense compounds in animal models of hepatitis, cancers, coronary artery restenosis and other diseases. The first antisense drug was recently approved by the FDA. This drug Fomivirsen, developed by Isis, is indicated for local treatment of cytomegalovirus in patients with AIDS who are intolerant of or have a contraindication to other treatments for CMV retinitis or who were insufficiently responsive to previous treatments for CMV retinitis.

Several antisense compounds are now in clinical trials is the United States. These include locally administered antivirals, systemic cancer therapeutics. Antisense therapeutics has the potential to treat many life-threatening diseases with a number of advantages over traditional drugs. Traditional drugs intervene after e disease-causing protein is formed. Antisense therapeutics, however, block mRNA transcription/translation and intervene before a protein is formed, and since antisense therapeutics target only one specific mRNA, they should be more effective with fewer side effects than current protein-inhibiting therapy.

A second option for disrupting gene expression at the level of transcription uses synthetic oligonucleotides capable of hybridizing with double stranded DNA. A triple helix is formed. Such oligonucleotides may prevent binding of transcription factors to the gene's promoter and therefore inhibit transcription. Alternatively, they may prevent duplex unwinding and, therefore, transcription of genes within the triple helical structure.

Thus, according to a further aspect of the present invention there is provided a pharmaceutical composition comprising the antisense oligonucleotide described herein and a pharmaceutically acceptable carrier. The pharmaceutically acceptable carrier can be, for example, a liposome loaded with the antisense oligonucleotide. Formulations for topical administration may include, but are not limited to, lotions, ointments, gels, creams, suppositories, drops, liquids, sprays and powders. Conventional pharmaceutical carriers, aqueous powder or oily bases, thickeners and the like may be necessary or desirable. Compositions for oral administration include powders or granules, suspensions or solutions in water or non aqueous media, sachets, capsules or tablets. Thickeners, diluents, flavorings, dispersing aids, emulsifiers or binders may be desirable. Formulations for parenteral administration map include, but are not limited to, sterile aqueous solutions which may also contain buffers, diluents and other suitable additives.

According to still a further aspect of the present invention there is provided a ribozyme comprising the antisense oligonucleotide described herein and a ribozyme sequence fused thereto. Such a ribozyme is readily synthesizable using solid phase oligonucleotide synthesis.

Ribozymes are being increasingly used for the sequence-specific inhibition of gene expression by the cleavage of mRNAs encoding proteins of interest. The possibility of designing ribozymes to cleave any specific target RNA has rendered them valuable tools in both basic research and therapeutic applications. In the therapeutics area, ribozymes have been exploited to target viral RNA3 in infectious diseases, dominant oncogenes in cancers and specific somatic mutations in genetic disorders. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C vital RNA in cell culture assays (Ribozyme Pharmaceuticals, Incorporated— WEB home page).

According to still a further aspect of the present invention there is provided a recombinant protein comprising a polypeptide (e) at least 50%, at least 60%, at least 65%, at least 70%, at least 75%, at least 80% at least 85%, at least 90%, at least 95% or preferably 95–100% homologous with SEQ ID NOs:2, 4, 6 or portions thereof as determined using the Bestfit procedure of the DNA sequence analysis software package developed by the Generic Computer Group (GCG) at the university of Wisconsin (gap creation penalty—50, gap extension penalty—3); (b) encoded by a polynucleotide at least 50%, at Least 60%, at least 65%, at least 70%, at least 75%, at least 80%, at least 85%, at least 90%, at least 95% or preferably 95–100% identical to SEQ ID NOs:1, 3, 5 or portions thereof as determined using the Bestfit procedure of the DNA sequence analysis software package developed by the Genetic Computer Group (GCG) at the university of Wisconsin (gap creation penalty—50, gap extension penalty—3); or (c) encoded by a polynucleotide hybridizable with SEQ ID NOs:1, 3, 5 or portions thereof at 65, 68 or 72° C. in 6×SSC, 1% SDS, 5×Denharts, 10% dextran sulfate, 100 μg/ml salmon sperm DNA, and $^{32}$p labeled probe and wash at 65, 68 or 72° C. with 3×SSC and 0.1% SDS or in addition with 0.1×SSC and 0.1% SDS.

Thus, this aspect of the present invention encompasses (i) polypeptides as set forth in SEQ ID NOs:2, 4 or 6; (ii) fragments thereof; (iii) polypeptides homologous thereto; and (iv) altered polypeptides characterized by mutations, such as deletion, insertion or substitution of one or more amino acids, either naturally occurring or man induced, either randomly or in a targeted fashion.

The polypeptide described herein is preferably capable of specifically binding HBV particles and to HBsAg preS1 protein or a portion thereof.

The recombinant protein according to the present invention is characterized by at least one of the following: (a) at least one EGF-like domain; (b) at least one transmembrane domain; (c) at least one site for attachment of a hydroxyl side chain; (d) a signal peptide; (e) an RGD attachment sequence; (f) at least one glycosylation site; and (g) at least one disulfide bond.

According to still a further aspect of the present invention there is provided a pharmaceutical composition comprising, as an active ingredient, the recombinant protein described herein and a pharmaceutical acceptable carrier which is further described above. Such a recombinant protein, when administered in vivo or in vitro, can protect against HBV attachment and infection.

According to another aspect of the present invention there is provided a peptide or a peptide analog comprising a stretch of at least 6, at least 7, at least 8, at least 9, at least 10, 10–15, 12–17, or 15–20 consecutive amino acids or analogs thereof derived from a polypeptide at least 50%, at least 55%, at least 60%, at least 65%, at least 70%, at least 75%, at least 80%, at least 85%, at least 90%, at least 95% or more, say 95%–100% identical or homologous (identical+similar) to SEQ ID NOs:2, 4 or 6 using as determined using the Bestfit procedure of the DNA sequence analysis software package developed by the Genetic Computer Group (GCG) at the university of Wisconsin (gap creation penalty—50, gap extension penalty—3). Preferably, the peptide or a peptide analog according to this aspect of the present invention comprises a stretch of at least 6, at least 7, at least 8, at least 9, at least 10, 10–15, 12–17, or 15–20 consecutive amino acids or analogs thereof derived from SEQ ID NOs:4, 5, 9 or 10.

As used herein in the specification and in the claims section below the phrase "derived from a polypeptide" refers to peptides derived from the specified protein or proteins and further to homologous peptides derived from equivalent regions of proteins homologous to the specified proteins of the same or other species. The term further relates to permissible amino acid alterations and peptidomimetics designed based on the amino acid sequence of the specified proteins or their homologous proteins.

As used herein in the specification and in the claims section below the term "amino acid" is understood to include the 20 naturally occurring amino acids; those amino acids often modified post-translationally in vivo, including for example hydroxyproline, phosphoserine and phosphothreonine; and other unusual amino acids including, but not limited to, 2-aminoadipic acid, hydroxylysine, isodesmosine, nor-valine, nor-leucine and ornithine. Furthermore, the term "amino acid" includes both D- and L-amino acids. Further elaboration of the possible amino acids usable according to the present invention and examples of non-natural amino acids are given hereinunder.

Hydrophilic aliphatic natural amino acids can be substituted by synthetic amino acids, preferably Nleu, Nval and/or α-aminobutyric acid or by aliphatic amino acids of the general formula —HN(CH$_2$)$_n$COOH, wherein n=3–5, as well as by branched derivatives thereof, such as, but not limited to:

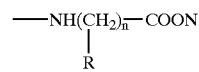

wherein R is, for example, methyl, ethyl or propyl, located at any one or more of the n carbons.

Each one, or more, of the amino acids can include a D-isomer thereof. Positively charged aliphatic carboxylic acids, such as, but not limited to, H$_2$N(CH$_2$)$_n$COOH, wherein n=2–4 and H$_2$N—C(NH)—NH(CH$_2$)$_n$COOH, wherein n=2–3, as well as by hydroxy Lysine, N-methyl Lysine or ornithine (Orn) can also be employed. Additionally, enlarged aromatic residues, such as, but not limited to, H$_2$N—(C$_6$H$_6$)—CH$_2$—COOH, p-aminophenyl alanine, H$_2$N—F(NH)—NH—(C$_6$H$_6$)—CH$_2$—COOH, p-guanidinophenyl alanine or pyridinoalanine (Pal) can also be employed.

Side chains of amino acid derivatives (if these are Ser, Tyr, Lys, Cys or Orn) can be protected-attached to alkyl, aryl alkyloyl or aryloyl moieties. Cyclic derivatives of amino acids can also be used. Cyclization can be obtained through amide bond formation, e.g., by incorporating Glu, Asp, Lys, Orn, di-amino butyric (Dab) acid, di-aminopropionic (Dap) acid at various positions in the chain (—CO—NH or —NH—CO bonds). Backbone to backbone cyclization can also be obtained through incorporation of modified amino acids of the formulas H—N((CH$_2$)$_n$—COOH)—C(R)H—COOH or H—N((CH$_2$)$_n$—COOH)—C(R)H—NH$_2$, wherein n=1–4, and further wherein R is any natural or non-natural side chain of an amino acid. Cyclization via formation of S—S bonds through incorporation of two Cys residues is also possible. Additional side-chain to side chain cyclization can be obtained via formation of an interaction bond of the formula —(—CH$_2$—)$_n$—S—CH$_2$—C—, wherein n=1 or 2, which is possible, for example, through incorporation of Cys or homoCys and reaction of its free SH group with, e.g., bromoacetylated Lys, Orn, Dab or Dap. Peptide bonds (—CO—NH—) within the peptide may be substituted by N-methylated bonds (—N(CH$_3$)—CO—), ester bonds (—C(R)H—C—O—O—C(R)—N—), ketomethylen bonds (—CO—CH$_2$—), α-aza bonds (—NH—N(R)—CO—), wherein R is any alkyl, e.g., methyl, carba bonds (—CH$_2$—NH—), hydroxyethylene bonds (—CH(OH)—CH$_2$—), thioamide bonds (—CS—NH—), olefinic double bonds (—CH=CH—), retro amide bonds (—NH—CO—), peptide derivatives (—N(R)—CH$_2$—CO—), wherein R is the "normal" side chain, naturally presented on the carbon atom. These modifications can occur at any of the bonds along the peptide chain and even at several (2–3) at the same time. Natural aromatic amino acids, Trp, Tyr and Phe, may be substituted for synthetic non-natural acid such as TIC, naphthylelanine (Nol), ring-methylated derivatives of Phe, halogenated derivatives of Phe or o-methyl-Tyr.

According to still another aspect of the present invention there is provided a display library comprising a plurality of display vehicles (such as phages, viruses or bacteria) each displaying at least 6, at least 7, at least 8, at least 9, at least 10, 10–15, 12–17, or 15–20 consecutive amino acids derived from a polypeptide at least 50%, at least 55%, at least 60%, at least 65%, at least 70%, at least 75%, at least 80%, at least 85%, at least 90%, at least 95% or more, say 95%–100% homologous (identical+similar) to SEQ ID NOs:2, 4 or 6 as determined using the Bestfit procedure of the DNA sequence analysis software package developed by the Genetic Computer Group (GCG) at the university of Wisconsin (gap creation penalty—50, gap extension penalty—3). According to a preferred embodiment of this aspect of the present invention substantially every 6, 7, 8, 9, 10, 10–15, 12–17 or 15–20 consecutive amino acids derived from the polypeptide described herein are displayed by at least one of the plurality of display vehicles, so as to provide a highly representative library. Preferably, the consecutive amino acids or amino acid analogs of the peptide or peptide analog according to this aspect of the present invention are derived from SEQ ID NOs:2, 4 or 6. Methods of constructing display libraries are well known in the art. such methods are described, for example, in Young A C, et al., "The three-dimensional structures of a polysaccharide binding antibody to *Cryptococcus neoformans* and its complex with a peptide from a phage display library: implications for the identification of peptide mimotopes" J Mol Biol Dec. 12, 1997; 274(4):622–34; Giebel L B et al. "Screening of cyclic peptide phage libraries identifies ligands that bind streptavidin with high affinities" Biochemistry Nov. 28, 1995; 34(47):15430–5; Davies E L et al., "Selection of specific phage-display antibodies using libraries derived from chicken immunoglobulin genes" J Immunol Methods Oct. 12, 1995; 186(1):125–35; Jones C. R. T. al. "Current trends in molecular recognition and bioseparation" J Chromatogr A Jul. 14, 1995; 707(1):3–22; Deng S J et al. "Basis for selection of improved carbohydrate-binding single-chain antibodies from synthetic gene libraries" Proc Natl Acad Sci USA May 23, 1995; 92(11):4992–6; and Deng S J et al. "Selection of antibody single-chain variable fragments with improved carbohydrate binding by phage display" J Biol Chem Apr. 1, 1994; 269(13):9533–8, which are incorporated herein by reference. Display libraries according to this aspect of the present invention can be used to identify and isolate polypeptides which are capable of regulating HBV attachment/infection e.g., in vivo. Thus, according to an additional aspect of the present invention there is provided a phage displaying at least a portion of the recombinant protein described herein, which can therefore be used, for example, as an anti-HBV medicament, either prophylactically or post infection.

According to still another aspect of the present invention there is provided an antibody comprising an immunoglobulin specifically recognizing and binding a polypeptide at least 50%, at least 55%, at least 60%, at least 65%, at least 70%, at least 75%, at least 80%, at least 85%, at least 90%, at least 95% or more, say 95%–100% homologous to SEQ ID NOs:2, 4 or 6 as determined using the Bestfit procedure of the DNA sequence analysis software package developed by the Genetic Computer Group (GCG) at the university of Wisconsin (gap creation penalty—50, gap extension penalty—3). According to a preferred embodiment of this aspect of the present invention the antibody specifically recognizing and binding the polypeptides set forth in SEQ ID NOs:2, 4 or 6.

The present invention can utilize serum immunoglobulins, polyclonal antibodies or fragments thereof, (i.e., immunoreactive derivative of an antibody), or monoclonal antibodies or fragments thereof. Monoclonal antibodies or purified fragments of the monoclonal antibodies having at least a portion of an antigen binding region, including such as Fv, F(ab)2, Fab fragments (Harlow and Lane, 1988 Antibody, Cold Spring Harbor), single chain antibodies (U.S. Pat. No. 4,946,778), chimeric or humanized antibodies and complementarily determining regions (CDR) may be prepared by conventional procedures. Purification of these serum immunoglobulins antibodies or fragments can be accomplished by a variety of methods known to those of skill including, precipitation by ammonium sulfate or sodium sulfate followed by dialysis against saline, ion exchange chromatography, affinity or immunoaffinity chromatography as well as gel filtration, zone electrophoresis, etc. (see Goding in, Monoclonal Antibodies: Principles and Practice, 2nd ed., pp. 104–126, 1986, Orlando, Fla., Academic Press). Under normal physiological conditions antibodies are found in plasma and other body fluids and in the membrane of certain cells and are produced by lymphocytes of the type denoted B cells or their functional equivalent. Antibodies of the IgG class are made up of four polypeptide chains linked together by disulfide bonds. The four chains of intact IgG molecules are two identical heavy chains referred to as H-chains and two identical light chains referred to as L-chains. Additional classes includes IgD, IgE, IgA, IgM and related proteins.

Methods for the generation and selection of monoclonal antibodies are well known in the art, as summarized for example in reviews such as Tramontano and Schloeder, Methods in Enzymology 178, 551–568, 1989. A recombinant protein of the present invention may be used to generate antibodies in vitro. More preferably, the recombinant protein of the present invention is used to elicit antibodies in vivo. In general, a suitable host animal is immunized with the recombinant protein of the present invention. Advantageously, the animal host used is a mouse of an inbred strain. Animals are typically immunized with a mixture comprising a solution of the recombinant protein of the present invention in a physiologically acceptable vehicle, and any suitable adjuvant, which achieves an enhanced immune response to the immunogen. By way of example, the primary immunization conveniently may be accomplished with a mixture of a solution of the recombinant protein of the present invention and Freund's complete adjuvant, said mixture being prepared in the form of a water in oil emulsion. Typically the immunization may be administered to the animals intramuscularly, intradermally, subcutaneously, intraperitoneally, into the footpads, or by any appropriate route of administration. The immunization schedule of the immunogen may be adapted as required, but customarily involves several subsequent or secondary immunizations using a milder adjuvant such as Freund's incomplete adjuvant. Antibody titers and specificity of binding to the protein can be determined during the immunization schedule by any convenient method including by way of example radioimmunoassay, or enzyme linked immunosorbant assay, which is known as the ELISA assay. When suitable antibody titers are achieved, antibody producing lymphocytes from the immunized animals are obtained, and these are cultured, selected and cloned, as is known in the art. Typically, lymphocytes may be obtained in large numbers from the spleens of immunized animals, but they may also be retrieved from the circulation, the lymph nodes or other lymphoid organs. Lymphocytes are then fused with any suitable myeloma cell line, to yield hybridomas, as is well known in the art. Alternatively, lymphocytes may also be stimulated to grow in culture, and may be immortalized by methods known in the art including the exposure of these lymphocytes to a virus, a chemical or a nucleic acid such as an oncogene, according to established protocols. After fusion, the hybridomas are cultured under suitable culture conditions, for example in multiwell plates, and the culture supernatants are screened to identify cultures containing antibodies that recognize the hapten of choice. Hybridomas that secrete antibodies that recognize the recombinant protein of the present invention are cloned by limiting dilution and expanded, under appropriate culture conditions. Monoclonal antibodies are purified and characterized in terms of immunoglobulin type and binding affinity.

According to yet an additional aspect of the present invention there is provided a method of isolating a polypeptide with HBV binding activity from a biological fluid. The method according to this aspect of the present invention is effected by (a) producing a purified HBV derived polypeptide; (b) binding the purified HBV derived polypeptide to a solid matrix to thereby obtain an affinity solid matrix; and (c) using the affinity solid matrix for affinity purification of the polypeptide with HBV binding activity from the biological fluid. According to a preferred embodiment of the method, the biological fluid is concentrated prior to step (c). The HBV derived polypeptide can be, for example, a HBV preS1 peptide or a portion thereof, which is suspected of involvement in attachment. Thus, for example, the HBV derived polypeptide can be as set forth in SEQ ID NO:8 or 9. The biological fluid employed is preferably urine, however, other fluids, such as serum, blood, nasal secretions, tears, saliva, etc. are also applicable.

According to still an additional aspect of the present invention there is provided a method of inhibiting HBV attachment to a hepatic cell. The method according to this aspect of the present invention is effected by exposing the cell to a recombinant urine derived protein, the recombinant urine derived protein being capable of binding to a purified HBV derived polypeptide. Accordingly, the present invention provides a pharmaceutical composition for inhibiting HBV attachment to a hepatic cell. The pharmaceutical composition comprising a recombinant urine derived protein, the recombinant urine derived protein being capable of binding to a purified HBV derived polypeptide, and a pharmaceutically acceptable carrier.

According to yet a further aspect of the present invention there is provided a method of inhibiting HBV attachment to a hepatic cell. The method according to this aspect of the present invention is effected by loading the cell with an antisense molecule being targeted against a mRNA encoding a recombinant urine derived protein, the recombinant urine derived protein being capable of binding to a purified HBV derived polypeptide. Accordingly, the present invention further provides a pharmaceutical composition for inhibiting HBV attachment to a hepatic cell the pharmaceutical composition comprising an antisense molecule being targeted against a mRNA encoding a recombinant urine derived protein, the recombinant urine derived protein being capable of binding to a purified HBV derived polypeptide, and a pharmaceutically acceptable carrier.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non-limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I–III Ausubel, R. M., ed. (1994); Cell Biology: A Laboratory Handbook" Volumes I–III Cellis, J. E., ed. (1994); "Current Protocols in Immunology" Volumes I–III Coligan J. E., ed. (1994); "Oligonucleotide Synthesis" Gait, M. J., ed. (1984); "Nucleic Acid Hybridization" Hames, B. D., and Higgins S. J., eds. (1985); "Transcription and Translation" Harnes, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods and Enzymology" Vol. 1–317 Academic Press; all of which are incorporated by reference as if fully set forth herein. Other general references are provided throughout this document. The procedures therein are believed to be well known in the art and are provided for the convenience of the reader. All the information contained therein is incorporated herein by reference.

Example 1

Materials and Methods

Preparation of the affinity columns: For the preparation of the affinity columns first a recombinant preS1 protein was prepared. The HBV preS1 gene was obtained by PCR amplification from a plasmid containing the entire HBV genome (cloned at the laboratory of W. J. Rutter at the UCSF). The following primers were used for amplification: 5'-GGAGATCTTCAAAACCTGGCAAAGGC-3' (SEQ ID NO:10) and 5'-GAATTCCACTGCATGGCCTG-3' (SEQ ID NO:11). The PCR product was cloned into the p-RSET-B vector (Invitrogene). The constructed plasmid was sequenced using the Weizmann Institute service center (see, SEQ ID NO:7). Recombinant His tagged pre-S1 protein (see SEQ ID NO:8) was expressed in $E.$ $coli$ B121 cells. Cells were grown overnight at 37° C. in M9ZB medium containing 0.4% glucose. The overnight culture was then diluted 1:50 with fresh M9ZB medium and was further grown at 37° C. When the OD (600 nm) reached 0.7–0.8 the cells were induced with IPTG (1 mM). The soluble fraction was purified to homogeneity from cell extracts with metal affinity chromatography using a Ninta-affinity column (Quiagene) and analyzed by SDS-PAGE.

A synthetic peptide affinity column was also prepared. A 29 amino-acid long peptide (SEQ ID NO:9) that was reported to be sufficient to interact with hepatocytes was synthesized at the Weizmann Institute service center. To obtain purified and homogenous peptide the synthetic peptide was further purified by gel filtration on a Sephadex G-25 column using 0.1 M NaOAc, pH 4.7, buffer. The purified fractions were stored at 4° C. until used.

For the preparation of the affinity column about 10 mg of either the recombinant preS1 protein or the synthetic peptide was covalently cross-linked to MSH activated beads Affinity-gel 10 (Bio-Rad) according to the manufacturer's instructions, and used for affinity chromatography.

Protein purification: Concentrated human urine (X 1000) was passed through the recombinant preS1 protein and/or the synthetic peptide affinity column, which were pre-equilibrated in PBS. The column was washed with PBS and then washed with 0.5 M NaCl, in order to wash out the non-specific associated proteins. The bound fraction was then eluted by a low pH buffer containing: 0.2 M glycine pH 2.5, 50% PEG and 10% TWEEN 20.

ELISA: ELISA plates were coated with preS1-affinity-purified proteins at varying dilution for 1 hour and then blocked with 0.05% gelatin for 30 minutes. 0.5 ng/ml HBsAg particles (obtained from Biotechnology general, Israel) were added to the immobilized proteins and incubated for 1 hour. Next, the plate was incubated with goat antibodies directed against HBsAg particles (diluted 1:2000) for 1 hour and for an additional hour with donkey anti goat antibodies (diluted 1:2500). All reactions were performed at 37° C.

Analysis of UP43: The UP43 was treated with N-glyconase that removes the sugar residues. Protein solution in TBS pH-8.0, 0.5% SDS and 50 mM β-Mercaptoethanol was boiled for 5 minutes. The protein sample was then brought to 0.25% of NP-40 and 0.3 units of N-glyconase was added and incubated overnight at 37° C. The reaction was stopped by boiling for 5 minutes and the protein was analyzed by a 12% SDS-PAGE.

cDNAs isolation:

UP43—RNA of Hep3B cells was subjected to RT-PCR reaction (Promega) using the following primers: For cDNA synthesis: 5'-GACTTGAATTCCTGTGGTTGA-3' (SEQ ID NO:12); for DNA amplification (PCR): 5'-GCCAGCACCATGGCAACCAGT-3' (SEQ ID NO:13) and 5'-GACTTGAATTCCTGTGGTTGA-3' (SEQ ID NO:14). The PCR product was digested with NcoI and EcoRI restriction enzymes (Fermentas) and cloned into the NcoI and EcoRI sites in the pRSET vector (Invitrogen). The sequence of the cloned PCR fragment was confirmed by DNA sequencing performed at the Weizmann Institute services center.

UP50—An EcoRI-BamHI fragment from I.M.A.G.E. clone number 12937 (Accession No. r16451) was labeled with $^{32}$P-dATP (Amersham, 3000 Ci/mmole) by nick translation. About $10^6$ cpm labeled probe was used to screen a human kidney gt10 cDNA library (obtained from O. Reiner at the Weizmann Institute, Israel) using standard plaque lifting and hybridization techniques. The inserts of positive plaques were rescued by PCR reaction, using phage derived primers. These fragments were cloned into pGEM-T vectors and sequences at the Weizmann. Another PCR reaction was employed, using a primer from up50 and a primer from the vector. The right clone was sequenced at the Weizmann Institute service center.

UPH1—See results section.

Construction of GFP chimera plasmids: up50 cDNA was cloned upstream to GFP in pEGFPN1 plasmid (clontech). Cos1 cells were transfected and the expression of the chimera protein was visualized by a florescent microscope.

Example 2

Production of the Recombinant HBV preS1 Protein

Based on previous research, the preS1 region of HBsAg is expected to contain the receptor binding region (Neurath et al., 1985; Petit et al., 1991). For HBV receptor purification a recombinant His-tagged preS1 protein (FIGS. 1a and 1b, SEQ ID NOs:7–8) was prepared. The recombinant protein was purified to homogeneity by employing a Ninta-affinity column (Quiagene). Also, a 29 amino-acid long peptide that was reported to be sufficient to interact with hepatocytes was synthesized (SEQ ID NO:9). This synthetic peptide was further purified on a G25 column to obtain a homogenous peptide (FIG. 1c).

Example 3

Purification of HBV preS1-binding Proteins

The recombinant preS1 protein (SEQ ID NO:7) was covalently cross-linked to beads (Affinity gel 10, BioRad) according to the manufacturer's instructions and was used for affinity chromatography. Concentrated urine (X 1000) was passed through the column, the column was washed and the bound proteins were eluted at low pH (see methods). The eluted fractions were analyzed on SDS-PAGE gel and silver stained. Two major bands appeared after elution from the preS1 column (FIG. 2, lane E2). The estimated molecular masses of the stained proteins were 50 and 43, and therefore they were named UP50 and UP43, respectively.

Example 4

The Purified Proteins Bind the preS1 Region with Receptor Binding Activity

Figure 3:
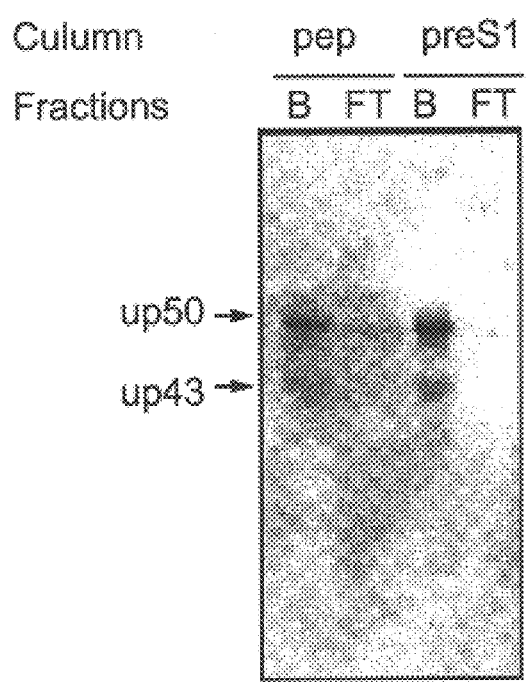
FIG. 3 is an SDS-PAGE silver stained gradient gel (5–20% of UP-proteins enrichment by the synthetic peptide preS(21–47) column. Urine proteins remaining on the recombinant preS1 protein column ware loaded on a second 21–47 synthetic peptide affinity column (pep) or on a preS1 recombinant affinity column (pre S1), as indicated. Majority of the UP50 and UP43 were retained on the column (fractions H) and barely seen in the follow-through (FT) fractions. UP50 was much more enriched than UP43. Molecular masse, (kDa) are indicated on the left by arrows.

Further purification of the proteins described in Example 2 was achieved by using a second affinity chromatography column, composed of the synthetic peptide that contain the preS1 amino-acids 21–49 region (FIGS. 1a and 1c). It has been reported that a similar synthetic peptide may block the attachment of HBV to hepatocytes, and therefore it is likely to contain the receptor binding sequence motif (Neurath et al., 1986). The eluted fractions were reloaded on a column that contained beads with cross-linked synthetic peptide, washed and eluted as for the first column. Both proteins, but especially UP50, were specifically retained on the column, indicating that they interact with the small preS1 region reported to be involved in hepatocyte binding (FIG. 3).

Example 5

The Affinity Purified Urine Proteins Bind HBV HBsAg Particles

Figure 4:
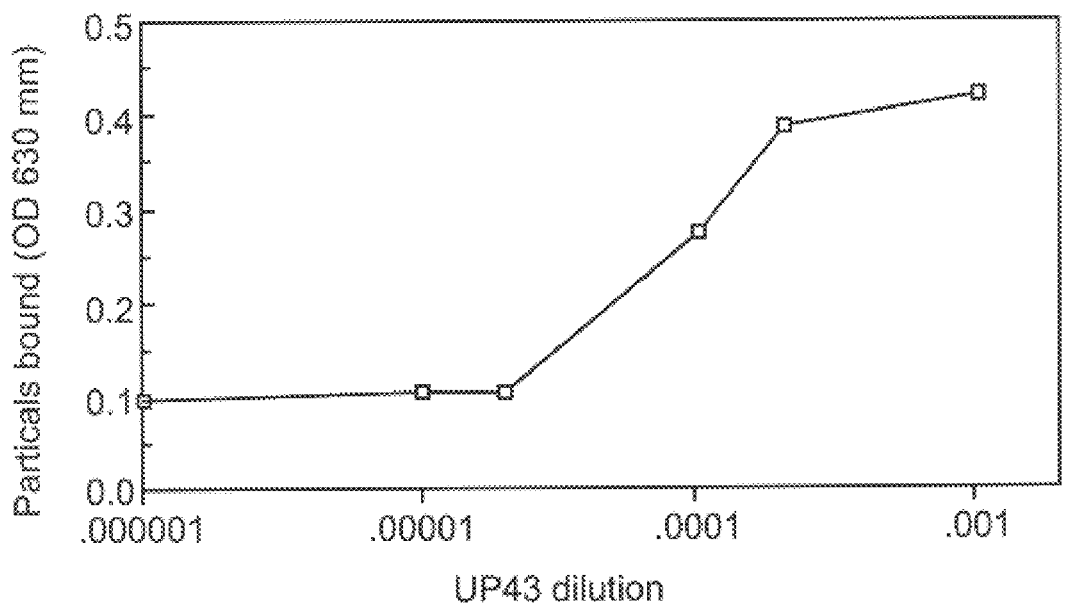
FIG. 4 demonstrates, using an ELISA test, that UP43 binds HBV HBsAg particles, ELISA plates were coated with affinity-purified UP43 at decreasing dilutions for 1 hour and that blocked with 0.05% gelatin for 30 minutes. 0.5 ng/ml HBV HBsAg particles were added to the immobilized UP43 and incubated for 1 hour. The plate was then incubated with goat antibodies against NBsAg particles (Biotechnology General, Israel) diluted 1:2000) for 1 hour and for an additional hour with horse radish peroxidase labeled donkey anti goat antibodies (diluted 1:2500). All reactions were performed at 3° C.

In order to test their capability to interact with HBsAg particles, ELISA was performed on immobilized affinity-purified urine proteins to which HBV particles had been added. As shown in FIG. 4, HBsAg particles interact with the affinity purified urine proteins, in a dose-dependent manner.

Example 6

The UP43 Protein is a Glycoprotein with Disulfide Bonds

Figure 5:
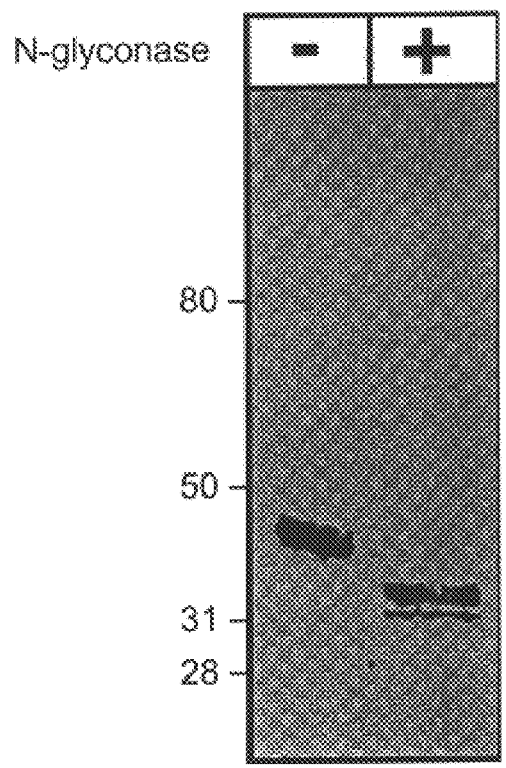
FIG. 5 shows an SDS-PAGE coomassie brilliant blue stained gel (12%) of UP43 either treated (+) or not treated (−) with N-glycanase over-night at 37° C. Molecular masses (kDa) are indicated on the left. Decreased size of UP43 after treatment demonstrates that it is a glycosylated protein.

After treatment with N-glyconase that removes sugar residues, the protein migration of UP43 was faster, indicating that it is a glycoprotein (FIG. 5). The fact that this protein (and also UP50, see below) are glycosylated suggests that they are secreted proteins. UP43's migration was slower in reduced gel than in non-reduced one. This indicates that the protein contains disulfide bonds.

Example 7

UP43 is an EGF-repeat Containing Protein

Microsequencing of four fragments of UP43 and isolation and sequencing of a full length cDNA thereof (SEQ ID NOs:1, 2 for cDNA and amino acids of UP43, respectively) revealed that it is identical to S1-5 (Databank accession No. AAA65590) published previously (FIG. 6). It has been shown that S1-5 is overexpressed in prematurely senescent Werner syndrome (WS) cells, in senescent and quiescent human diploid fibroblasts (HDF) (Lecka et al., 1995). The S1-5 transcript, when injected into cells, causes stimulation of DNA synthesis. Four distinct cDNA fragments containing ATG codons in the same ORF suggest that there is an alternative initiation of translation/splicing in the 5' end, allowing the synthesis of four different UP43 proteins in the calculated molecular weights range of 54.6 kDa to 43.1 kDa (Lecka-Czernik et al., 1995).

The proteins include five to six epidermal growth factor (EGF)-like domains, depending on the choice of translational start site (Doolittle et al., 1984). This domain is defined by the spacing of six conserved cysteins over a sequence of 35–40 amino acids. The six cysteines form three disulfide bonds. The proteins further includes an N-glycosylation site at Asn-249, as was confirmed by biochemical tests. A highly hydrophobic sequence of 14 amino acids was found at the C-terminus of the proteins, which could serve as a transmembrane domain. The putative proteins further contain a hydrophobic amino acid sequence at their N terminus, which may serve as a secretory signal peptide, and a possible signal sequence cleavage site. These findings suggest that the proteins translated from the up43 gene are membrane-associated.

Example 8

Cellular Localization of UP50

Figure 7:
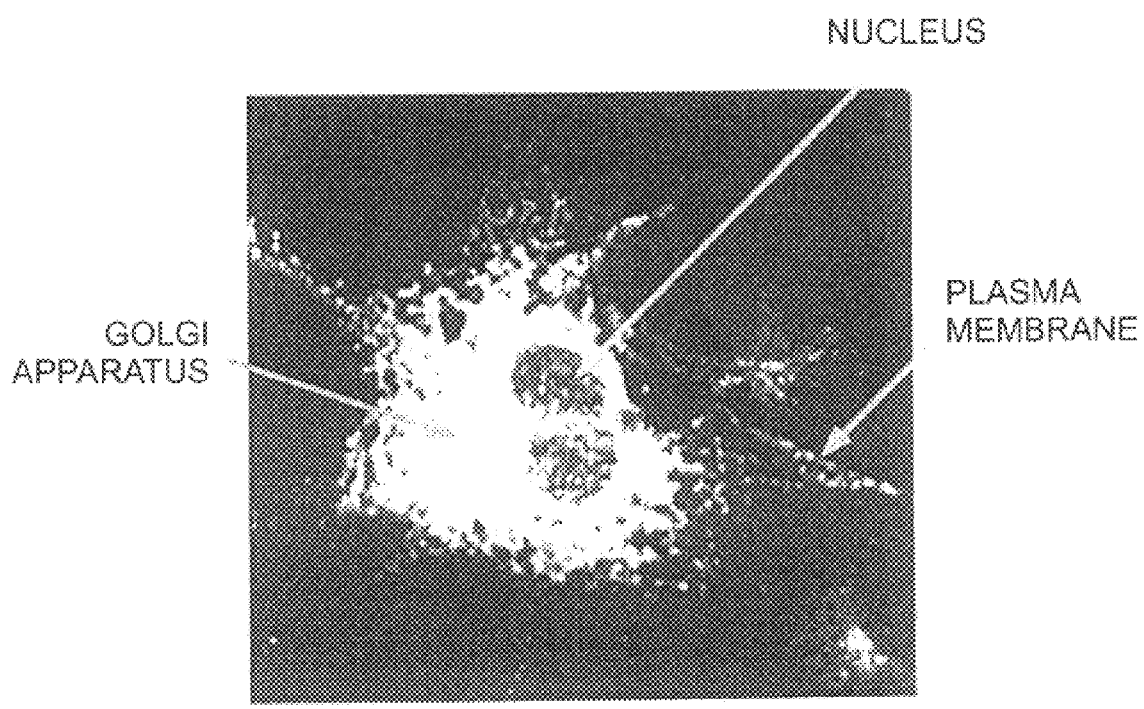
FIG. 7 demonstrates UP50-GFP location within cells. Cost cells were transfected with a UP50-GFP plasmid (see Example 1 of the Examples section) and the transfected cells were visualized by confocal laser scanning microscopy.

In order to determine the localization of UP50 in the cell, up50 cDNA was fused with the Green Fluorescence Protein (GFP) cDNA. Thus a cDNA fragment encoding a GFP, of 27 kDa molecular mass, was fused to a up50 cDNA, such that the in the fused protein product the GFP amino acid sequence is located at the C terminus of UP50, so as not to disrupt the putative secretory signal at the N terminus. The construct was transfected to Cos1 cells. UP50-GFL was localized on cell membrane (FIG. 7) confirming the membrane association suggested in Example 6.

Example 9

UP50 is an EGF-repeat Containing Protein and is Similar to UP43

Four peptides derived from trypsin digested UP50 were sequenced. These peptides are underlined in FIG. 8. The peptides showed 100% identity to the translation product of an I.M.A.G.E. clone (clone number 12937), which was ordered and sequenced. The clone contained only about 300 coding nucleotides. Consequently, isolation of the complete up50 cDNA was accomplished and its sequence determined (FIG. 8, SEQ ID NOs:3, 4 for cDNA and amino acids of UP50, respectively). Inspection of the amino acid sequence of the C-terminus of UP50 revealed a region homologous to the C-terminus of UP43. In addition, UP50 migration was slower in reduced gel than in non-reduced one (data not shown), indicating that the protein contains disulfide bonds similar to those found in UP43. The sequences of up50 and UP50 revealed that this is a novel gene.

Example 10

Pattern of up50 Expression

Figure 9A:
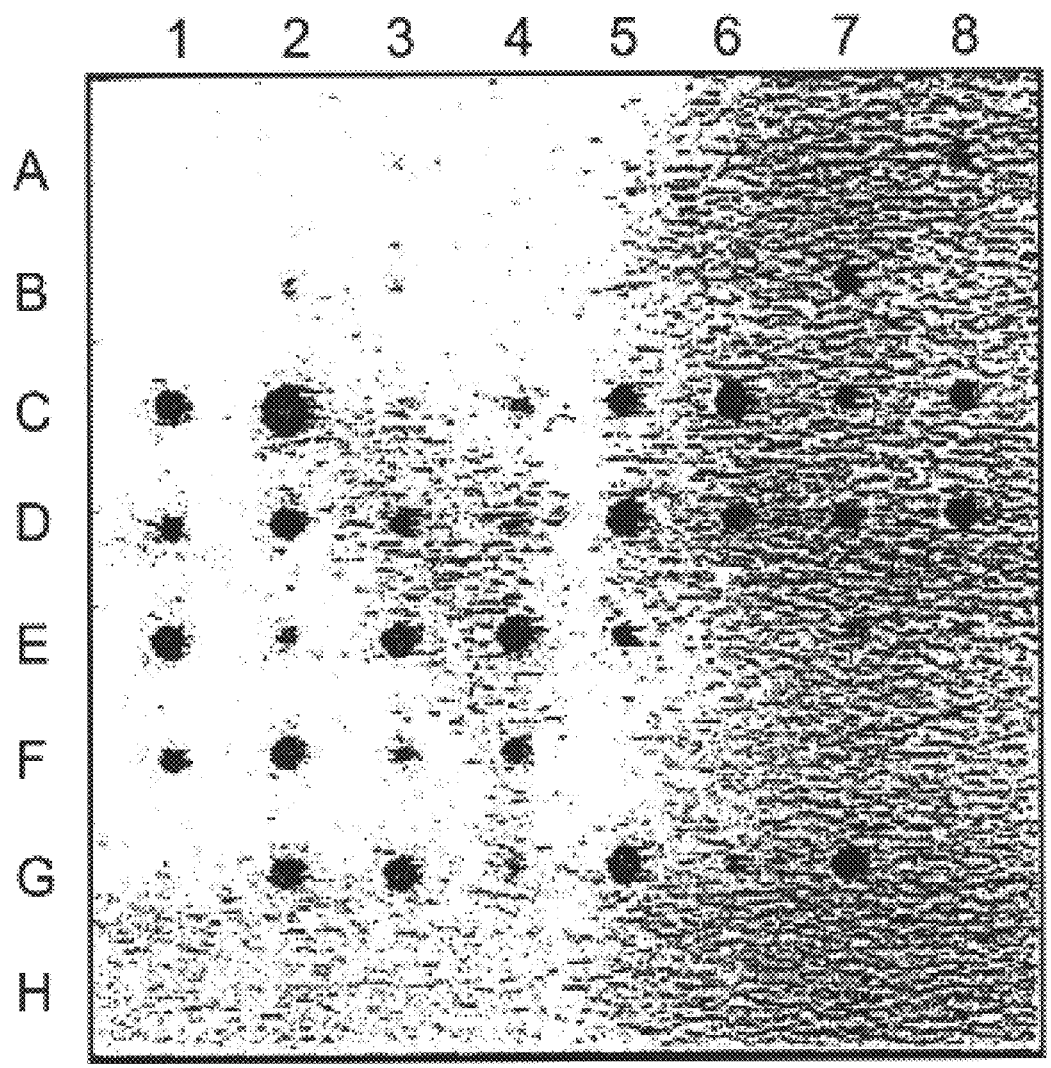

To determine the tissue specificity of up50 expression, a commercial "master-blot" (Clontech) that contains an equal and normalized amount of RNA from different adult and fetal tissues was employed. up50 cDNA was $^{32}$p labeled by random priming and as incubated with this blot in a hybridization reaction. Although up50 is expressed in many adult and fetal tissues, there are some differences at the level of expression (FIGS. 9a and 9b). The highest level of expression was obtained in aorta (square 2C of the grid in FIG. 9a) and the lowest in brain, medulla oblongata and spinal cord.

A similar analysis was done with a up43 probe (data not shown) and the results were similar but not identical to those obtained with the up50 probe. For example, expression of up43 can be easily detected in the different brain regions. Of particular interest is the liver, where expression of these proteins is moderate. The fact that these proteins are expressed in many tissues argues strongly against them being exclusively responsible for liver recognition by HBV. Therefore, a role of co-factor is attributed to these proteins. This situation is similar to that of the CD4 receptor in HIV infection. CD4 receptor is not sufficient for infection as cofactors are required for infection. In the case of HIV, a chemokine family of proteins which is ubiquitously expressed in T cells plays the role of cofactor.

Example 11

UPH1, a UP50 Homolog

A close and novel UP50 homologue was found screening the EST database (Databank accession No. r16451, FIG. 10) and was named UP homologue 1 (UPH1). The EST clone, of which only 600 bp, 300 at each prime, were known was ordered and sequenced. It included the full cDNA (SEQ ID NOs:5, 6 for UPH1 cDNA and amino acids, respectively). The sequence of UPH1 revealed that unlike UP50, it does not include an RGD motif and therefore it is unlikely to interact with fibronectin, otherwise it includes the other motifs found in the UP family, as is further described herein.

The homology between the amino (upper right homology (identity)), SEQ ID NOs:2, 4 and 6) and nucleic (lower left, identity, SEQ ID NOs:1, 3 and 5) acids sequences of UP43, UP50 and UPH1 and the cDNA sequences encoding same, respectively, are given in the following Table:

|      | UP43 | UP50      | UPH1        |
|------|------|-----------|-------------|
| UP43 | —    | 53 (44.2) | 58.1 (49.9) |
| UP50 | 52.8 | —         | 60.5 (50.3) |
| UPH1 | 55.7 | 59.1      | —           |

Example 12

General Features of UP43, UP50 and UPH1

Figure 11:
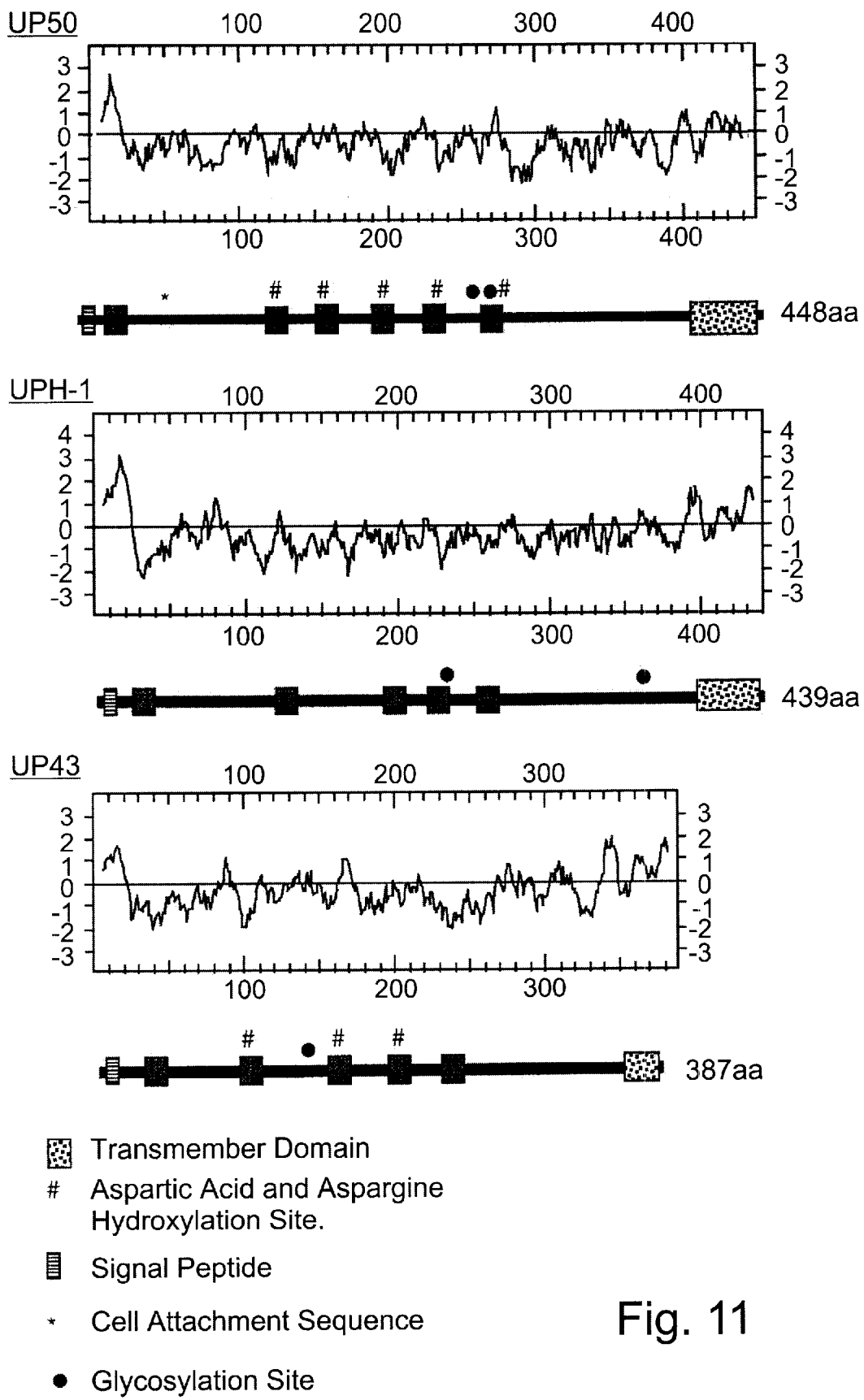
FIG. 11 shows hydrophobicity plots of the three proteins UP50) UPH1, and UP43 as well as schematic representations of amino acid sequences indicating transmembrane domains, hydroxylation sites, signal peptide domains, cell attachment sequences, glycosylation sites, and EGF like domains.

All the UP proteins contain similar EGF repeats of a calcium binding type found in numerous other proteins, such as described in Davis, 1990. Also, some EGF repeats contain aspartic-acid and asparagine that undergo hydroxylation (FIG. 11). All UP proteins have a transmembrane domain at the C-terminus, suggesting that they are membrane associated. They also contain a signal-peptide (the highly hydrophobic region) at the N-terminus, suggesting that the N-terminus is positioned out of the cells (FIG. 11).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

REFERENCES

1. Davis, C. G. 1990. The many faces of epidermal growth factor repeats. New Biol 2: 410–9.
2. De, M. S., Z. J. Gong, W. Suwandhi, P. J. van A. Soumillion and S. H. Yap. 1997. Organ and species specificity of hepatitis B virus (HBV) infection: a review of literature with a special reference to preferential attachment of HBV to human hepatocytes. J Viral Hepat 4: 145–53.
3. Doolittle, R. F., D. F. Feng and M. S. Johnson. 1984. Computer-based characterization of epidermal growth factor precursor. Nature 307: 558–60.
4. Lecka-Czernik, B., Jr., Lumpkin, C. K., and S. Goldstein. 1995. An overexpressed gene transcript in senescent and quiescent human fibroblasts encoding a novel protein in the epidermal growth factor-like repeat family stimulates DNA synthesis. Mol Cell Biol 15: 120–8.
5. Neurath, A. R., S. B. Kent, N. Strick, P. Taylor and C. E. Stevens. 1985. Hepatitis B virus contains pre-S gene-encoded domains. Nature 315: 154–6.
6. Neurath, A. R., S. B. Kent, K. Parker, A. M. Prince, N. Strick, B. Brotman and P. Sproul. 1986. Antibodies to a synthetic peptide from the preS 120–145 region of the hepatitis B virus envelope are virus neutralizing. Vaccine 4: 35–7.
7. Petit, M. A., S. Dubanchet, F. Capel, P. Voet, C. Dauguet and P. Hauser. 1991. HepG2 cell binding activities of different hepatitis B virus isolates: inhibitory effect of anti-HBs and anti-preS1 (21–47). Virology 180: 483–91.
8. Shouval, D., Y. Ilan, R. Adler, R. Deepen, A. Panet, Z. Even-Chen, M. Gorecki and W. H. Gerlich. 1994. Improved immunogenicity in mice of a mammalian cell-derived recombinant hepatitis B vaccine containing pre-S1 and pre-S2 antigens as compared with conventional yeast-derived vaccines. Vaccine 12: 1453–9.

What is claimed is:

1. A method of inhibiting HBV attachment to a hepatic cell the method comprising exposing the cell to a polypeptide capable of binding the preS1 region of HBV and having an amino acid sequence at least 90% homologous to the amino acid sequence set forth in SEQ ID NO:2 as determined using the Bestfit software of the GCG package set with a gap creation penalty of 50 and a gap extension penalty of 3, thereby inhibiting HBV attachment to a hepatic cell.

2. The method of claim 1, wherein said polypeptide is as set forth in SEQ ID NO:2.

* * * * *

SEQUENCE LISTING

<160> NUMBER OF SEQ ID NOS: 14

<210> SEQ ID NO 1
<211> LENGTH: 2512
<212> TYPE: DNA
<213> ORGANISM: Homo sapiens

<400> SEQUENCE: 1

```
caatgcactg acggatatga gtgggatcct gtgagacagc aatgcaaaga tattgatgaa      60
tgtgacattg tcccagacgc ttgtaaaggt ggaatgaagt gtgtcaacca ctatggagga     120
tacctctgcc ttccgaaaac agcccagatt attgtcaata atgaacagcc tcagcaggaa     180
acacaaccag cagaaggaac ctcagggca accaccgggg ttgtagctgc cagcagcatg      240
gcaaccagtg gagtgttgcc cgggggtggt tttgtggcca gtgctgctgc agtcgcaggc     300
cctgaaatgc agactggccg aaataacttt gtcatccggc ggaacccagc tgaccctcag     360
cgcattccct ccaaccccttc ccaccgtatc cagtgtgcag caggctacga gcaaagtgaa     420
cacaacgtgt gccaagacat agacgagtgc actgcaggga cgcacaactg tagagcagac     480
caagtgtgca tcaatttacg gggatccttt gcatgtcagt gccctcctgg atatcagaag     540 cgagggggagc agtgcgtaga catagatgaa tgtaccatcc ctccatattg ccaccaaaga     600
tgcgtgaata caccaggctc attttattgc cagtgcagtc ctgggtttca attggcagca     660
aacaactata cctgcgtaga tataaatgaa tgtgatgcca gcaatcaatg tgctcagcag     720
tgctacaaca ttcttggttc attcatctgt cagtgcaatc aaggatatga gctaagcagt     780
gacaggctca actgtgaaga cattgatgaa tgcagaacct caagctacct gtgtcaatat     840
caatgtgtca atgaacctgg gaaattctca tgtatgtgcc cccagggata ccaagtggtg     900
agaagtagaa catgtcaaga tataaatgag tgtgagacca caaatgaatg ccgggaggat     960
gaaatgtgtt ggaattatca tggcggcttc cgttgttatc cacgaaatcc ttgtcaagat    1020
ccctacattc taacaccaga gaaccgatgt gtttgcccag tctcaaatgc catgtgccga    1080
gaactgcccc agtcaatagt ctacaaatac atgagcatcc gatctgatag gtctgtgcca    1140
tcagacatct tccagataca ggccacaact atttatgcca acaccatcaa tacttttcgg    1200
attaaatctg gaatgaaaa tggagagttc tacctacgac aaacaagtcc tgtaagtgca    1260
atgcttgtgc tcgtgaagtc attatcagga ccaagagaac atatcgtgga cctggagatg    1320
```

-continued

```
ctgacagtca gcagtatagg gaccttccgc acaagctctg tgttaagatt gacaataata    1380
gtggggccat tttcatttta gtcttttcta agagtcaacc acaggcattt aagtcagcca    1440
aagaatattg ttaccttaaa gcactatttt atttatagat atatctagtg catctacatc    1500
tctatactgt acactcaccc ataacaaaca attacaccat ggtataaagt gggcatttaa    1560
tatgtaaaga ttcaaagttt gtctttatta ctatatgtaa attagacatt aatccactaa    1620
actggtcttc ttcaagagag ctaagtatac actatctggt gaaacttgga ttctttccta    1680
taaaagtggg accaagcaat gatgatcttc tgtggtgctt aaggaaactt actagagctc    1740
cactaacagt ctcataagga ggcagccatc ataaccattg aatagcatgc aagggtaaga    1800
atgagttttt aactgctttg taagaaaatg gaaaaggtca ataaagatat atttctttag    1860
aaaatgggga tctgccatat ttgtgttggt ttttattttc atatccagcc taaaggtggt    1920
tgtttattat atagtaataa atcattgctg tacaacatgc tggtttctgt agggtatttt    1980
taattttgtc agaaatttta gattgtgaat attttgtaaa aaacagtaag caaaattttc    2040
cagaattccc aaaatgaacc agataccccc tagaaaatta tactattgag aaatctatgg    2100
ggaggatatg agaaaataaa ttccttctaa accacattgg aactgacctg aagaagcaaa    2160
ctcggaaaat ataataacat ccctgaattc aggcattcac aagatgcaga acaaaatgga    2220 taaaggtat ttcactggag aagttttaat ttctaagtaa aatttaaatc ctaacacttc    2280
actaatttat aactaaaatt tctcatcttc gtacttgatg ctcacagagg aagaaaatga    2340
tgatggtttt tattcctggc atccagagtg acagtgaact taagcaaatt accctcctac    2400
ccaattctat ggaatatttt atacgtctcc ttgtttaaaa tctgactgct ttactttgat    2460
gtatcatatt tttaaataaa aataaatatt cctttagaag atcactctaa aa             2512
```

<210> SEQ ID NO 2
<211> LENGTH: 387
<212> TYPE: PRT
<213> ORGANISM: Homo sapiens

<400> SEQUENCE: 2

```
Met Ala Thr Ser Gly Val Leu Pro Gly Gly Phe Val Ala Ser Ala
1               5                   10                  15

Ala Ala Val Ala Gly Pro Glu Met Gln Thr Gly Arg Asn Asn Phe Val
                20                  25                  30

Ile Arg Arg Asn Pro Ala Asp Pro Gln Arg Ile Pro Ser Asn Pro Ser
            35                  40                  45

His Arg Ile Gln Cys Ala Ala Gly Tyr Glu Gln Ser Glu His Asn Val
        50                  55                  60

Cys Gln Asp Ile Asp Glu Cys Thr Ala Gly Thr His Asn Cys Arg Ala
65                  70                  75                  80

Asp Gln Val Cys Ile Asn Leu Arg Gly Ser Phe Ala Cys Gln Cys Pro
                85                  90                  95

Pro Gly Tyr Gln Lys Arg Gly Glu Gln Cys Val Asp Ile Asp Glu Cys
            100                 105                 110

Thr Ile Pro Pro Tyr Cys His Gln Arg Cys Val Asn Thr Pro Gly Ser
        115                 120                 125

Phe Tyr Cys Gln Cys Ser Pro Gly Phe Gln Leu Ala Ala Asn Asn Tyr
    130                 135                 140

Thr Cys Val Asp Ile Asn Glu Cys Asp Ala Ser Asn Gln Cys Ala Gln
145                 150                 155                 160

Gln Cys Tyr Asn Ile Leu Gly Ser Phe Ile Cys Gln Cys Asn Gln Gly
```

```
                      165                 170                 175
Tyr Glu Leu Ser Ser Asp Arg Leu Asn Cys Glu Asp Ile Asp Glu Cys
                180                 185                 190

Arg Thr Ser Ser Tyr Leu Cys Gln Tyr Gln Cys Val Asn Glu Pro Gly
            195                 200                 205

Lys Phe Ser Cys Met Cys Pro Gln Gly Tyr Gln Val Val Arg Ser Arg
        210                 215                 220

Thr Cys Gln Asp Ile Asn Glu Cys Glu Thr Thr Asn Glu Cys Arg Glu
225                 230                 235                 240

Asp Glu Met Cys Trp Asn Tyr His Gly Gly Phe Arg Cys Tyr Pro Arg
                245                 250                 255

Asn Pro Cys Gln Asp Pro Tyr Ile Leu Thr Pro Glu Asn Arg Cys Val
            260                 265                 270

Cys Pro Val Ser Asn Ala Met Cys Arg Glu Leu Pro Gln Ser Ile Val
        275                 280                 285

Tyr Lys Tyr Met Ser Ile Arg Ser Asp Arg Ser Val Pro Ser Asp Ile
    290                 295                 300

Phe Gln Ile Gln Ala Thr Thr Ile Tyr Ala Asn Thr Ile Asn Thr Phe
305                 310                 315                 320

Arg Ile Lys Ser Gly Asn Glu Asn Gly Glu Phe Tyr Leu Arg Gln Thr
                325                 330                 335

Ser Pro Val Ser Ala Met Leu Val Leu Val Lys Ser Leu Ser Gly Pro
            340                 345                 350

Arg Glu His Ile Val Asp Leu Glu Met Leu Thr Val Ser Ser Ile Gly
        355                 360                 365

Thr Phe Arg Thr Ser Ser Val Leu Arg Leu Thr Ile Ile Val Gly Pro
    370                 375                 380

Phe Ser Phe
385

<210> SEQ ID NO 3
<211> LENGTH: 2019
<212> TYPE: DNA
<213> ORGANISM: Homo sapiens
<220> FEATURE:
<221> NAME/KEY: misc_feature
<222> LOCATION: (22)..(22)
<223> OTHER INFORMATION: any nucleotide

<400> SEQUENCE: 3
accccggcgc tctccccgtg tnctctccac gactcgctcg gcccctctgg aataaaacac      60
ccgcgagccc cgagggccca gaggaggccg acgtgcccga gctcctccgg gggtcccgcc     120
cgcaagcttt cttctcgcct tcgcatctcc tcctcgcgcg tcttggacat gccaggaata     180 aaaggatac tcactgttac cattctggct ctctgtcttc caagccctgg gaatgcacag     240
gcacagtgca cgaatggctt tgacctggat cgccagtcag acagtgtttt agatattgat     300
gaatgccgaa ccatcccga ggcctgccga ggagacatga tgtgtgttaa ccaaaatggg     360
gggtatttat gccattcccg acaaaccct gtgtatcgag ggccctactc gaacccctac     420
tcgaccccct actcaggtcc gtacccagca gctgccccac cactctcagc tccaaactat     480
cccacgatct ccaggcctct tatatgccgc tttggatacc agatggatga agcaaccaa     540 tgtgtggatg tggacgagtg tgcaacagat tcccaccagt gcaacccac ccagatttgc     600 atcaatatga agggcgggta cacctgctcc tgcaccgacg gatattggct tttggaaggc     660
cagtgcttag acattgatga atgtcgctat ggttactgcc agcagctctg tgcgaatgtt     720
```

-continued

```
cctggatcct attcttgtac atgcaaccct ggttttaccc tcaatgagga tggaaggtct    780
tgccaagatg tgaacgagtg tgccaccgag aacccctgcg tgcaaacctg cgtcaacacc    840
tacggctctt tcatctgccg ctgtgaccca ggatatgaac ttgaggaaga tggcgttcat    900
tgcagtgata tggacgagtg cagcttctct gagttcctct gccaacatga gtgtgtgaac    960
cagcccggca catacttctg ctcctgccct ccaggctaca tcctgctgga tgacaaccga   1020
agctgccaag acatcaacga atgtgagcac aggaaccaca cgtgcaacct gcagcagacg   1080
tgctacaatt tacaaggggg cttcaaatgc atcgacccca tccgctgtga ggagccttat   1140
ctgaggatca gtgataaccg ctgtatgtgt cctgctgaga accctggctg cagagaccag   1200
cccttttacca tcttgtaccg ggacatggac gtggtgtcag gacgctccgt tcccgctgac   1260
atcttccaaa tgcaagccac gacccgctac cctggggcct attacatttt ccagatcaaa   1320
tctgggaatg agggcagaga attttacatg cggcaaacgg gccccatcag tgccaccctg   1380
gtgatgacac gccccatcaa agggccccgg gaaatccagc tggacttgga aatgatcact   1440
gtcaacactg tcatcaactt cagaggcagc tccgtgatcc gactgcggat atatgtgtcg   1500
cagtacccat tctgagcctc gggctggagc ctccgacgct gcctctcatt ggcaccaagg   1560
gacaggagaa gagaggaaat aacagagaga atgagagcga cacagacgtt aggcatttcc   1620
tgctgaacgt tttccccgaag agtcagcccc gacttcctga ctctcacctg tactattgca   1680
gacctgtcac cctgcaggac ttgccacccc agttcctat gacacagtta tcaaaaagta   1740
ttatcattgc tcccctgata gaagattgtt ggtgaatttt caaggccttc agtttatttc   1800
cactattttc aaagaaaata gattaggttt gcgggggtct gagtctatgt tcaaagactg   1860
tgaacagctt gctgtcactt cttcacctct tccactcctt ctctcactgt gttactgctt   1920
tgcaaagacc cggggagctg gcggggaaac cctggggagt agctagtttg cttttttgcgt   1980
acacagaaga aggctatgta aacaaaccac agcaggatc                           2019
```

<210> SEQ ID NO 4
<211> LENGTH: 448
<212> TYPE: PRT
<213> ORGANISM: Homo sapiens

<400> SEQUENCE: 4

```
Met Pro Gly Ile Lys Arg Ile Leu Thr Val Thr Ile Leu Ala Leu Cys
1               5                   10                  15

Leu Pro Ser Pro Gly Asn Ala Gln Ala Gln Cys Thr Asn Gly Phe Asp
            20                  25                  30

Leu Asp Arg Gln Ser Gly Gln Cys Leu Asp Ile Asp Glu Cys Arg Thr
        35                  40                  45

Ile Pro Glu Ala Cys Arg Gly Asp Met Met Cys Val Asn Gln Asn Gly
    50                  55                  60

Gly Tyr Leu Cys His Ser Arg Thr Asn Pro Val Tyr Arg Gly Pro Tyr
65                  70                  75                  80

Ser Asn Pro Tyr Ser Thr Pro Tyr Ser Gly Pro Tyr Pro Ala Ala Ala
                85                  90                  95

Pro Pro Leu Ser Ala Pro Asn Tyr Pro Thr Ile Ser Arg Pro Leu Ile
            100                 105                 110

Cys Arg Phe Gly Tyr Gln Met Asp Glu Ser Asn Gln Cys Val Asp Val
        115                 120                 125

Asp Glu Cys Ala Thr Asp Ser His Gln Cys Asn Pro Thr Gln Ile Cys
    130                 135                 140
```

```
Ile Asn Met Lys Gly Gly Tyr Thr Cys Ser Cys Thr Asp Gly Tyr Trp
145                 150                 155                 160

Leu Leu Glu Gly Gln Cys Leu Asp Ile Asp Glu Cys Arg Tyr Gly Tyr
            165                 170                 175

Cys Gln Gln Leu Cys Ala Asn Val Pro Gly Ser Tyr Ser Cys Thr Cys
            180                 185                 190

Asn Pro Gly Phe Thr Leu Asn Glu Asp Gly Arg Ser Cys Gln Asp Val
            195                 200                 205

Asn Glu Cys Ala Thr Glu Asn Pro Cys Val Gln Thr Cys Val Asn Thr
210                 215                 220

Tyr Gly Ser Phe Ile Cys Arg Cys Asp Pro Gly Tyr Glu Leu Glu Glu
225                 230                 235                 240

Asp Gly Val His Cys Ser Asp Met Asp Glu Cys Ser Phe Ser Glu Phe
                245                 250                 255

Leu Cys Gln His Glu Cys Val Asn Gln Pro Gly Thr Tyr Phe Cys Ser
                260                 265                 270

Cys Pro Pro Gly Tyr Ile Leu Leu Asp Asp Asn Arg Ser Cys Gln Asp
                275                 280                 285

Ile Asn Glu Cys Glu His Arg Asn His Thr Cys Asn Leu Gln Gln Thr
290                 295                 300

Cys Tyr Asn Leu Gln Gly Gly Phe Lys Cys Ile Asp Pro Ile Arg Cys
305                 310                 315                 320

Glu Glu Pro Tyr Leu Arg Ile Ser Asp Asn Arg Cys Met Cys Pro Ala
                325                 330                 335

Glu Asn Pro Gly Cys Arg Asp Gln Pro Phe Thr Ile Leu Tyr Arg Asp
                340                 345                 350

Met Asp Val Val Ser Gly Arg Ser Val Pro Ala Asp Ile Phe Gln Met
                355                 360                 365

Gln Ala Thr Thr Arg Tyr Pro Gly Ala Tyr Tyr Ile Phe Gln Ile Lys
            370                 375                 380

Ser Gly Asn Glu Gly Arg Glu Phe Tyr Met Arg Gln Thr Gly Pro Ile
385                 390                 395                 400

Ser Ala Thr Leu Val Met Thr Arg Pro Ile Lys Gly Pro Arg Glu Ile
                405                 410                 415

Gln Leu Asp Leu Glu Met Ile Thr Val Asn Thr Val Ile Asn Phe Arg
                420                 425                 430

Gly Ser Ser Val Ile Arg Leu Arg Ile Tyr Val Ser Gln Tyr Pro Phe
            435                 440                 445
```

<210> SEQ ID NO 5
<211> LENGTH: 1661
<212> TYPE: DNA
<213> ORGANISM: Homo sapiens

<400> SEQUENCE: 5

| | | | |
|---|---|---|---|
| atgctcccct gcgcctcctg cctacccggg tctctactgc tctgggcgct gctactgttg | 60 |
| ctcttgggat cagcttctcc tcaggattct gaagagcccg acagctacac ggaatgcaca | 120 |
| gatggctata cccagacagc caactgccgg gatgtcaacg agtgtctgac catccctgag | 180 |
| gcctgcaagg gggaaatgaa gtgcatcaac cactacgggg gctacttgtg cctgccccgc | 240 |
| tccgctgccg tcatcaacga cctacacggc gagggacccc cgccaccagt gcctcccgtc | 300 |
| aacacccaac ccctgcccac aggctatgag cccgacgatc aggacagctg tgtggatgtg | 360 |
| gacgagtgtg cccaggccct gcacgactgt cgccccagcc aggactgcca taacttgcct | 420 |

-continued

```
ggctcctatc agtgcacctg ccctgatggt taccgcaaga tcgggcccga gtgtgtggac    480
atagacgagt gccgctaccg ctactgccag caccgctgcg tgaacctgcc tggctccttc    540
cgctgccagt gcgagccggg cttccagctg gggcctaaca accgctcctg tgttgatgtg    600
aacgagtgtg acatgggggc cccatgcgag cagcgctgct tcaactccta tgggaccttc    660
ctgtgtcgct gccaccaggg ctatgagctg catcgggatg gcttctcctg cagtgatatt    720
gatgagtgta gctactccag ctacctctgt cagtaccgct gcgtcaacga gccaggccgt    780
ttctcctgcc actgcccaca gggttaccag ctgctggcca cacgcctctg ccaagacatt    840
gatgagtgtg agtctggtgc gcaccagtgg tccgaggccc aaacctgtgt caatttccat    900
gggggctacc gctgcgtgga caccaaccgc tgcgtggagc cctacatcca ggtctctgag    960
aaccgctgtc tctgcccggc ctccaaccct ctatgtcgag agcagccttc atccattgtg   1020
caccgctaca tgaccatcac ctcggaagcg agagacccg ctgacgtgtt ccagatccag   1080
gcgacctccg tctaccccgg tgcctacaat gcctttcaga tccgtgctgg aaactcgcag   1140
gggactttt acattaggca aatcaacaac gtcagcgcca tgctggtcct cgcccggccg   1200
gttacgggcc cccgggagta cgtgctggac ctggagatgg tcaccatgaa ttccctcatg   1260
agctaccggg ccagctctgt actgaggctc accgtctttg tagggcccta caccttctga   1320
ggagcaggag ggagccaccc tccctgcagc taccctagct gaggagcctg ttgtgagggg   1380
cagaatgaga aaggcccagg ggcccccatt gacaggagct gggagctctg caccacgagc   1440
ttcagtcacc ccgagaggag aggaggtaac gaggagggcg gacttccags cccsgsccag   1500
agatttggac ttggctggct tgcaggggtc ctaagaaact ccactctgga cagcgccagg   1560
aggccctggg ttccattcct aactctgcct caaactgtac atttggataa gccctagtag   1620
ttccctgggc ctgtttttct ataaaacgag gcaactggaa a                       1661
```

<210> SEQ ID NO 6
<211> LENGTH: 439
<212> TYPE: PRT
<213> ORGANISM: Homo sapiens

<400> SEQUENCE: 6

```
Met Leu Pro Cys Ala Ser Cys Leu Pro Gly Ser Leu Leu Leu Trp Ala
1               5                   10                  15

Leu Leu Leu Leu Leu Gly Ser Ala Ser Pro Gln Asp Ser Glu Glu
            20                  25                  30

Pro Asp Ser Tyr Thr Glu Cys Thr Asp Gly Tyr Thr Gln Thr Ala Asn
        35                  40                  45

Cys Arg Asp Val Asn Glu Cys Leu Thr Ile Pro Glu Ala Cys Lys Gly
    50                  55                  60

Glu Met Lys Cys Ile Asn His Tyr Gly Gly Tyr Leu Cys Leu Pro Arg
65                  70                  75                  80

Ser Ala Ala Val Ile Asn Asp Leu His Gly Glu Gly Pro Pro Pro
                85                  90                  95

Val Pro Pro Val Asn Thr Gln Pro Leu Pro Thr Gly Tyr Glu Pro Asp
            100                 105                 110

Asp Gln Asp Ser Cys Val Asp Val Asp Glu Cys Ala Gln Ala Leu His
        115                 120                 125

Asp Cys Arg Pro Ser Gln Asp Cys His Asn Leu Pro Gly Ser Tyr Gln
    130                 135                 140

Cys Thr Cys Pro Asp Gly Tyr Arg Lys Ile Gly Pro Glu Cys Val Asp
```

```
                145                 150                 155                 160
Ile Asp Glu Cys Arg Tyr Arg Tyr Cys Gln His Arg Cys Val Asn Leu
                    165                 170                 175
Pro Gly Ser Phe Arg Cys Gln Cys Glu Pro Gly Phe Gln Leu Gly Pro
                180                 185                 190
Asn Asn Arg Ser Cys Val Asp Val Asn Glu Cys Asp Met Gly Ala Pro
                195                 200                 205
Cys Glu Gln Arg Cys Phe Asn Ser Tyr Gly Thr Phe Leu Cys Arg Cys
            210                 215                 220
His Gln Gly Tyr Glu Leu His Arg Asp Gly Phe Ser Cys Ser Asp Ile
225                 230                 235                 240
Asp Glu Cys Ser Tyr Ser Ser Tyr Leu Cys Gln Tyr Arg Cys Val Asn
                245                 250                 255
Glu Pro Gly Arg Phe Ser Cys His Cys Pro Gln Gly Tyr Gln Leu Leu
            260                 265                 270
Ala Thr Arg Leu Cys Gln Asp Ile Asp Glu Cys Glu Ser Gly Ala His
            275                 280                 285
Gln Trp Ser Glu Ala Gln Thr Cys Val Asn Phe His Gly Gly Tyr Arg
    290                 295                 300
Cys Val Asp Thr Asn Arg Cys Val Glu Pro Tyr Ile Gln Val Ser Glu
305                 310                 315                 320
Asn Arg Cys Leu Cys Pro Ala Ser Asn Pro Leu Cys Arg Glu Gln Pro
                325                 330                 335
Ser Ser Ile Val His Arg Tyr Met Thr Ile Thr Ser Glu Ala Glu Arg
                340                 345                 350
Pro Ala Asp Val Phe Gln Ile Gln Ala Thr Ser Val Tyr Pro Gly Ala
                355                 360                 365
Tyr Asn Ala Phe Gln Ile Arg Ala Gly Asn Ser Gln Gly Asp Phe Tyr
    370                 375                 380
Ile Arg Gln Ile Asn Asn Val Ser Ala Met Leu Val Leu Ala Arg Pro
385                 390                 395                 400
Val Thr Gly Pro Arg Glu Tyr Val Leu Asp Leu Glu Met Val Thr Met
                405                 410                 415
Asn Ser Leu Met Ser Tyr Arg Ala Ser Ser Val Leu Arg Leu Thr Val
                420                 425                 430
Phe Val Gly Ala Tyr Thr Phe
            435

<210> SEQ ID NO 7
<211> LENGTH: 534
<212> TYPE: DNA
<213> ORGANISM: Artificial sequence
<220> FEATURE:
<223> OTHER INFORMATION: HBV derived insertion cloned in p-RSET- B

<400> SEQUENCE: 7
atgcggggtt ctcatcatca tcatcatcat ggtatggcta gcatgactgg tggacagcaa    60
atgggtcggg atctgtacga cgatgacgat aaggatccga gctcgagatc ttcaaaacct   120
cgcaaaggca tggggacgaa tctttctgtt cccaatcctc tgggattctt tcccgatcat   180
cagttggacc ctgcattcgg agccaactca acaatccag attgggactt caaccccgtc    240
aaggacgact ggccagcagc caaccaagta ggagtgggag cattcgggcc aaggctcacc   300
cctccacacg gcggtatttt ggggtggagc cctcaggctc aggcatatt gaccacagtg    360
tcaacaattc ctcctcctgc ctccaccaat cggcagtcag gaaggcagcc tactcccatc   420
```

```
tctccacctc taagagacag tcatcctcag gccatgcagt ggaattcgaa gcttgatccg    480
gctgctaaca agcccgaaa ggaagctgag ttggctgctg ccaccgctga gcaa           534
```

<210> SEQ ID NO 8
<211> LENGTH: 178
<212> TYPE: PRT
<213> ORGANISM: Artificial sequence
<220> FEATURE:
<223> OTHER INFORMATION: HBV derived recombinant protein

<400> SEQUENCE: 8

```
Met Arg Gly Ser His His His His His Gly Met Ala Ser Met Thr
1               5                   10                  15

Gly Gly Gln Gln Met Gly Arg Asp Leu Tyr Asp Asp Asp Lys Asp
                20                  25                  30

Pro Ser Ser Arg Ser Ser Lys Pro Arg Lys Gly Met Gly Thr Asn Leu
        35                  40                  45

Ser Val Pro Asn Pro Leu Gly Phe Phe Pro Asp His Gln Leu Asp Pro
    50                  55                  60

Ala Phe Gly Ala Asn Ser Asn Asn Pro Asp Trp Asp Phe Asn Pro Val
65                  70                  75                  80

Lys Asp Asp Trp Pro Ala Ala Asn Gln Val Gly Val Gly Ala Phe Gly
                85                  90                  95

Pro Arg Leu Thr Pro Pro His Gly Gly Ile Leu Gly Trp Ser Pro Gln
            100                 105                 110

Ala Gln Gly Ile Leu Thr Thr Val Ser Thr Ile Pro Pro Pro Ala Ser
        115                 120                 125

Thr Asn Arg Gln Ser Gly Arg Gln Pro Thr Pro Ile Ser Pro Pro Leu
    130                 135                 140

Arg Asp Ser His Pro Gln Ala Met Gln Trp Asn Ser Lys Leu Asp Pro
145                 150                 155                 160

Ala Ala Asn Lys Ala Arg Lys Glu Ala Glu Leu Ala Ala Ala Thr Ala
                165                 170                 175

Glu Gln
```

<210> SEQ ID NO 9
<211> LENGTH: 29
<212> TYPE: PRT
<213> ORGANISM: Artificial sequence
<220> FEATURE:
<223> OTHER INFORMATION: Synthetic peptide

<400> SEQUENCE: 9

```
Pro Leu Gly Phe Phe Pro Asp His Gln Leu Asp Pro Ala Phe Gly Ala
1               5                   10                  15

Asn Ser Asn Asn Pro Asp Trp Asp Phe Asn Pro Gly Lys
                20                  25
```

<210> SEQ ID NO 10
<211> LENGTH: 26
<212> TYPE: DNA
<213> ORGANISM: Artificial sequence
<220> FEATURE:
<223> OTHER INFORMATION: Synthetic oligonucleotide

<400> SEQUENCE: 10

```
ggagatcttc aaaacctggc aaaggc                                         26
```

-continued

```
<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
gaattccact gcatggcctg                                              20

<210> SEQ ID NO 12
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 12
gacttgaatt cctgtggttg a                                            21

<210> SEQ ID NO 13
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 13
gccagcacca tggcaaccag t                                            21

<210> SEQ ID NO 14
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 14
gacttgaatt cctgtggttg a                                            21
```